(12) United States Patent
Seibel et al.

(10) Patent No.: US 8,537,203 B2
(45) Date of Patent: Sep. 17, 2013

(54) SCANNING BEAM WITH VARIABLE SEQUENTIAL FRAMING USING INTERRUPTED SCANNING RESONANCE

(75) Inventors: Eric Seibel, Seattle, WA (US); Richard Johnston, Sammamish, WA (US); Brandon Tuttle, Sacramento, CA (US)

(73) Assignee: University of Washington, Seattle, WA (US)

( * ) Notice: Subject to any disclaimer, the term of this patent is extended or adjusted under 35 U.S.C. 154(b) by 1006 days.

(21) Appl. No.: 12/088,057

(22) PCT Filed: Nov. 23, 2005

(86) PCT No.: PCT/US2005/042577
§ 371 (c)(1),
(2), (4) Date: Jul. 14, 2008

(87) PCT Pub. No.: WO2007/067163
PCT Pub. Date: Jun. 14, 2007

(65) Prior Publication Data
US 2009/0028407 A1 Jan. 29, 2009

(51) Int. Cl.
*H04N 13/00* (2006.01)
*H04N 15/00* (2006.01)
*A61B 1/04* (2006.01)

(52) U.S. Cl.
USPC .................. 348/45; 385/15; 359/201.1

(58) Field of Classification Search
USPC ........... 600/407; 606/5; 546/285; 356/318; 385/25; 235/462.39, 462.42; 359/201.1
See application file for complete search history.

(56) References Cited

U.S. PATENT DOCUMENTS

| 4,118,270 A | 10/1978 | Pan et al. ............... 156/659 |
| 4,234,788 A | 11/1980 | Palmer et al. .......... 250/227 |
| 4,265,699 A | 5/1981 | Ladany ................... 156/657 |

(Continued)

FOREIGN PATENT DOCUMENTS

| DE | 4428967 | 12/1995 |
| EP | 0 713 672 | 5/1996 |

(Continued)

OTHER PUBLICATIONS

Barnard et al., "Mode Transforming Properties of Tapered Single-mode Fiber Microlens." *Appl. Opt.* vol. 32, No. 12: 2090-2094, Apr. 20, 1993.

(Continued)

*Primary Examiner* — Dustin Nguyen
(74) *Attorney, Agent, or Firm* — Wilson Sonsini Goodrich & Rosati

(57) ABSTRACT

A scanning device for use in an endoscope or other applications can be driven to scan a region with one or more different scanning parameters during successive scanning frames. The scanning device, which can include an optical fiber or reflective surface driven by an actuator to move relative to one or more axes, can be provided with a drive signal that is different during successive scanning frames so that the scanning pattern can be caused to differ between the successive scanning frames by one or more of size, amplitude in at least one direction, depth, duration, shape, and resolution. Thus, different scanning frames can be employed for imaging, carrying out a diagnosis, rendering a therapy, and/or monitoring a site, using the appropriate scanning pattern, appropriate light source, and other parameters for each function that is carried out by the scanning device.

39 Claims, 18 Drawing Sheets

(56) References Cited

U.S. PATENT DOCUMENTS

| | | | |
|---|---|---|---|
| 4,410,235 A | 10/1983 | Klement et al. | 350/96.18 |
| 4,454,547 A | 6/1984 | Yip et al. | 358/293 |
| 4,686,963 A | 8/1987 | Cohen et al. | 128/4 |
| 4,688,555 A | 8/1987 | Wardle | 128/4 |
| 4,695,163 A | 9/1987 | Schachar | 356/369 |
| 4,710,619 A | 12/1987 | Haberl | 250/203 |
| 4,743,283 A | 5/1988 | Borsuk | 65/2 |
| 4,758,222 A | 7/1988 | McCoy | 604/95 |
| 4,762,118 A | 8/1988 | Lia et al. | 128/4 |
| 4,768,513 A | 9/1988 | Suzuki | 128/634 |
| 4,782,228 A | 11/1988 | Westell | 250/236 |
| 4,804,395 A | 2/1989 | Clark et al. | 65/2 |
| 4,824,195 A | 4/1989 | Khoe | 350/96.18 |
| 4,850,364 A | 7/1989 | Leavitt | 128/661.09 |
| 4,928,316 A | 5/1990 | Heritage et al. | 455/600 |
| 4,979,496 A | 12/1990 | Komi | 128/4 |
| 4,983,165 A | 1/1991 | Loiterman | 604/95 |
| 5,037,174 A | 8/1991 | Thompson | 385/33 |
| 5,074,642 A | 12/1991 | Hicks | 385/116 |
| 5,103,497 A | 4/1992 | Hicks | 385/117 |
| 5,172,685 A | 12/1992 | Nudelman | 128/6 |
| 5,209,117 A | 5/1993 | Bennett | 73/517 |
| 5,231,286 A | 7/1993 | Kajimura et al. | 250/234 |
| 5,247,174 A | 9/1993 | Berman | 250/235 |
| 5,272,330 A | 12/1993 | Betzig et al. | 250/216 |
| 5,286,970 A | 2/1994 | Betzig et al. | 250/227.26 |
| 5,305,759 A | 4/1994 | Kaneko et al. | 600/476 |
| 5,321,501 A | 6/1994 | Swanson et al. | 356/345 |
| 5,360,968 A | 11/1994 | Scott | 235/454 |
| 5,381,782 A | 1/1995 | DeLaRama et al. | 128/4 |
| 5,394,500 A | 2/1995 | Marchman | 385/123 |
| 5,405,337 A | 4/1995 | Maynard | 604/281 |
| 5,425,123 A | 6/1995 | Hicks | 385/117 |
| 5,459,803 A | 10/1995 | Yamane et al. | 385/33 |
| 5,480,046 A | 1/1996 | Filas et al. | 216/7 |
| 5,507,725 A | 4/1996 | Savage et al. | 604/95 |
| 5,512,035 A | 4/1996 | Konstorum et al. | 600/146 |
| 5,535,759 A | 7/1996 | Wilk | 128/898 |
| 5,549,542 A | 8/1996 | Kovalcheck | 600/146 |
| 5,563,969 A | 10/1996 | Honmou | 385/35 |
| 5,570,441 A | 10/1996 | Filas et al. | 385/43 |
| 5,627,922 A | 5/1997 | Kopelman et al. | 385/12 |
| 5,643,175 A | 7/1997 | Adair | 600/133 |
| 5,649,897 A | 7/1997 | Nakamura | 600/141 |
| 5,663,550 A * | 9/1997 | Peng | 235/462.39 |
| 5,668,644 A | 9/1997 | Kuroiwa et al. | 358/480 |
| 5,703,979 A | 12/1997 | Filas et al. | 385/43 |
| 5,715,337 A | 2/1998 | Spitzer et al. | 385/4 |
| 5,724,169 A | 3/1998 | LaGasse | 359/173 |
| 5,727,098 A | 3/1998 | Jacobson | 385/31 |
| 5,735,276 A * | 4/1998 | Lemelson | 600/407 |
| 5,765,561 A | 6/1998 | Chen et al. | 128/653.1 |
| 5,770,737 A * | 6/1998 | Reinhardt et al. | 546/285 |
| 5,894,122 A | 4/1999 | Tomita | 250/234 |
| 5,906,620 A | 5/1999 | Nakao et al. | 606/113 |
| 5,919,200 A | 7/1999 | Stambaugh et al. | 606/159 |
| 5,939,709 A | 8/1999 | Ghislain et al. | 250/216 |
| 5,947,905 A | 9/1999 | Hadjicostis et al. | 600/463 |
| 5,984,860 A | 11/1999 | Shan | 600/116 |
| 5,991,697 A | 11/1999 | Nelson et al. | 702/49 |
| 6,035,229 A | 3/2000 | Silverstein et al. | 600/473 |
| 6,046,720 A | 4/2000 | Melville et al. | 345/108 |
| 6,069,698 A | 5/2000 | Ozawa et al. | 356/345 |
| 6,081,605 A | 6/2000 | Roth et al. | 382/103 |
| 6,091,067 A | 7/2000 | Drobot et al. | 250/234 |
| 6,096,054 A | 8/2000 | Wyzgala et al. | 606/170 |
| 6,097,528 A | 8/2000 | Lebby et al. | 359/251 |
| 6,134,003 A | 10/2000 | Tearney et al. | 356/345 |
| 6,142,957 A | 11/2000 | Diamond et al. | 600/567 |
| 6,148,095 A | 11/2000 | Prause et al. | 382/131 |
| 6,161,035 A | 12/2000 | Furusawa | 600/476 |
| 6,169,281 B1 | 1/2001 | Chen et al. | 250/234 |
| 6,185,443 B1 | 2/2001 | Crowley | 600/407 |
| 6,191,862 B1 | 2/2001 | Swanson et al. | 356/450 |
| 6,203,538 B1 * | 3/2001 | Peyman | 606/5 |
| 6,211,904 B1 | 4/2001 | Adair et al. | 348/76 |
| 6,215,437 B1 | 4/2001 | Schurmann et al. | 342/42 |
| 6,240,312 B1 | 5/2001 | Alfano et al. | 600/476 |
| 6,241,657 B1 | 6/2001 | Chen et al. | 600/117 |
| 6,246,914 B1 | 6/2001 | de la Rama et al. | 607/122 |
| 6,289,144 B1 | 9/2001 | Neuschafer et al. | 385/12 |
| 6,294,775 B1 | 9/2001 | Seibel et al. | 250/208.1 |
| 6,327,493 B1 | 12/2001 | Ozawa et al. | 600/476 |
| 6,370,422 B1 | 4/2002 | Richards-Kortum et al. | 600/478 |
| 6,387,119 B2 | 5/2002 | Wolf et al. | 623/1.11 |
| 6,441,359 B1 | 8/2002 | Cozier et al. | 250/216 |
| 6,443,894 B1 | 9/2002 | Sumanaweera et al. | 600/443 |
| 6,461,337 B1 | 10/2002 | Minotti et al. | 604/264 |
| 6,466,687 B1 | 10/2002 | Uppaluri et al. | 382/128 |
| 6,485,413 B1 | 11/2002 | Boppart et al. | 600/160 |
| 6,515,274 B1 | 2/2003 | Moskovits et al. | 250/216 |
| 6,515,781 B2 | 2/2003 | Lewis et al. | 359/204 |
| 6,525,310 B2 | 2/2003 | Dunfield | 250/235 |
| 6,545,260 B1 | 4/2003 | Katashiro | 250/227.26 |
| 6,546,271 B1 | 4/2003 | Reisfeld | 600/407 |
| 6,549,801 B1 | 4/2003 | Chen et al. | 600/425 |
| 6,550,918 B1 | 4/2003 | Agostinelli et al. | 353/7 |
| 6,563,105 B2 | 5/2003 | Seibel et al. | 250/208.1 |
| 6,563,998 B1 | 5/2003 | Farah et al. | 385/131 |
| 6,564,087 B1 | 5/2003 | Pitris et al. | 600/478 |
| 6,564,089 B2 | 5/2003 | Izatt et al. | 600/478 |
| 6,612,980 B2 | 9/2003 | Chen et al. | 600/117 |
| 6,615,072 B1 | 9/2003 | Izatt et al. | 600/478 |
| 6,678,541 B1 | 1/2004 | Durkin et al. | 600/310 |
| 6,685,718 B1 | 2/2004 | Wyzgala et al. | 606/170 |
| 6,687,010 B1 | 2/2004 | Horii et al. | 356/479 |
| 6,689,064 B2 | 2/2004 | Hager et al. | 600/454 |
| 6,690,963 B2 | 2/2004 | Ben-Haim et al. | 600/424 |
| 6,694,983 B2 | 2/2004 | Wolf et al. | 128/898 |
| 6,735,463 B2 | 5/2004 | Izatt et al. | 600/476 |
| 6,755,532 B1 | 6/2004 | Cobb | 353/7 |
| 6,773,394 B2 | 8/2004 | Taniguchi et al. | 600/117 |
| 6,779,892 B2 | 8/2004 | Agostinelli et al. | 353/7 |
| 6,785,571 B2 | 8/2004 | Glossop | 600/424 |
| 6,788,967 B2 | 9/2004 | Ben-Haim et al. | 600/424 |
| 6,818,001 B2 | 11/2004 | Wulfman et al. | 606/159 |
| 6,826,342 B1 | 11/2004 | Bise et al. | 385/125 |
| 6,832,984 B2 | 12/2004 | Stelzer et al. | 604/93.01 |
| 6,836,560 B2 | 12/2004 | Emery | 382/145 |
| 6,839,586 B2 | 1/2005 | Webb | 600/478 |
| 6,845,190 B1 | 1/2005 | Smithwick et al. | 385/25 |
| 6,856,712 B2 | 2/2005 | Fauver et al. | 385/12 |
| 6,858,005 B2 | 2/2005 | Ohline et al. | 600/141 |
| 6,872,433 B2 | 3/2005 | Seward et al. | 428/36.9 |
| 6,882,429 B1 | 4/2005 | Weitekamp et al. | 356/482 |
| 6,889,175 B2 | 5/2005 | Green | 702/190 |
| 6,892,090 B2 | 5/2005 | Verard et al. | 600/424 |
| 6,895,270 B2 | 5/2005 | Ostrovsky | 600/476 |
| 6,902,528 B1 | 6/2005 | Garibaldi et al. | 600/118 |
| 6,932,829 B2 | 8/2005 | Majercak | 606/198 |
| 6,975,898 B2 | 12/2005 | Seibel | 600/473 |
| 7,004,173 B2 | 2/2006 | Sparks et al. | 128/898 |
| 7,023,558 B2 | 4/2006 | Fee et al. | 356/489 |
| 7,038,191 B2 | 5/2006 | Kare et al. | 250/227.11 |
| 7,072,046 B2 | 7/2006 | Xie et al. | 356/479 |
| 7,158,234 B2 | 1/2007 | Uchiyama et al. | 356/479 |
| 7,170,610 B2 | 1/2007 | Knuttel | 356/456 |
| 7,179,220 B2 | 2/2007 | Kukuk | 600/118 |
| 7,189,961 B2 | 3/2007 | Johnston et al. | 250/234 |
| 7,236,283 B2 | 6/2007 | Kikuchi et al. | |
| 7,252,674 B2 | 8/2007 | Wyzgala et al. | 606/170 |
| 7,261,687 B2 | 8/2007 | Yang | 600/173 |
| 7,310,174 B2 * | 12/2007 | Wine et al. | 359/201.1 |
| 7,324,211 B2 | 1/2008 | Tsujita | 356/497 |
| 7,349,098 B2 | 3/2008 | Li et al. | 356/479 |
| 7,366,376 B2 | 4/2008 | Shishkov et al. | 385/35 |
| 7,404,929 B2 | 7/2008 | Fulghum, Jr. | 422/82.05 |
| 7,428,997 B2 * | 9/2008 | Wiklof et al. | 235/462.42 |
| 7,447,408 B2 | 11/2008 | Bouma et al. | 385/123 |
| 7,515,274 B2 | 4/2009 | Gelikonov et al. | 356/479 |
| 7,530,948 B2 | 5/2009 | Seibel et al. | 600/102 |
| 7,615,005 B2 | 11/2009 | Stefanchik et al. | 600/106 |
| 7,616,986 B2 | 11/2009 | Seibel et al. | 600/476 |
| 7,747,312 B2 | 6/2010 | Barrick et al. | 600/426 |

| | | | |
|---|---|---|---|
| 7,783,337 B2 | 8/2010 | Feldman et al. | 600/160 |
| 2001/0030744 A1 | 10/2001 | Chang et al. | 356/73 |
| 2001/0055462 A1 | 12/2001 | Seibel | |
| 2002/0064341 A1* | 5/2002 | Fauver et al. | 385/25 |
| 2002/0071625 A1 | 6/2002 | Bartholomew et al. | 385/12 |
| 2002/0149769 A1* | 10/2002 | Roorda et al. | 356/318 |
| 2003/0009189 A1 | 1/2003 | Gilson et al. | 606/200 |
| 2003/0032878 A1 | 2/2003 | Shahidi | 600/429 |
| 2003/0045778 A1 | 3/2003 | Ohline et al. | 600/114 |
| 2003/0055317 A1 | 3/2003 | Taniguchi et al. | 600/117 |
| 2003/0103199 A1 | 6/2003 | Jung et al. | 356/73 |
| 2003/0103665 A1 | 6/2003 | Uppaluri et al. | 382/131 |
| 2003/0142934 A1 | 7/2003 | Pan et al. | 385/116 |
| 2003/0160721 A1 | 8/2003 | Gilboa et al. | 342/450 |
| 2003/0179428 A1 | 9/2003 | Suzuki et al. | 359/204 |
| 2003/0208107 A1 | 11/2003 | Refael | 600/300 |
| 2003/0208134 A1 | 11/2003 | Secrest et al. | 600/562 |
| 2003/0216639 A1 | 11/2003 | Gilboa et al. | 600/424 |
| 2003/0220749 A1 | 11/2003 | Chen et al. | 702/31 |
| 2003/0236564 A1 | 12/2003 | Majercak | 623/1.11 |
| 2004/0015049 A1 | 1/2004 | Zarr | 600/101 |
| 2004/0015053 A1 | 1/2004 | Bieger et al. | 600/117 |
| 2004/0033006 A1 | 2/2004 | Farah | 385/14 |
| 2004/0061072 A1 | 4/2004 | Gu et al. | 250/458.1 |
| 2004/0118415 A1 | 6/2004 | Hall et al. | 128/898 |
| 2004/0147827 A1 | 7/2004 | Bowe | 600/374 |
| 2004/0176683 A1 | 9/2004 | Whitin et al. | 600/424 |
| 2004/0181148 A1 | 9/2004 | Uchiyama et al. | 600/425 |
| 2004/0199052 A1 | 10/2004 | Banik et al. | 600/142 |
| 2004/0243227 A1 | 12/2004 | Starksen et al. | 623/2.11 |
| 2004/0249267 A1 | 12/2004 | Gilboa | 600/204 |
| 2004/0260199 A1 | 12/2004 | Hardia et al. | 600/566 |
| 2005/0020878 A1 | 1/2005 | Ohnishi et al. | 600/117 |
| 2005/0020926 A1 | 1/2005 | Wiklof et al. | 600/476 |
| 2005/0036150 A1 | 2/2005 | Izatt et al. | 356/479 |
| 2005/0054931 A1 | 3/2005 | Clark | 600/453 |
| 2005/0065433 A1 | 3/2005 | Anderson | 600/424 |
| 2005/0085693 A1 | 4/2005 | Belson et al. | 600/146 |
| 2005/0111009 A1 | 5/2005 | Keightley et al. | 356/602 |
| 2005/0168751 A1 | 8/2005 | Horii et al. | 356/479 |
| 2005/0171438 A1 | 8/2005 | Chen et al. | 600/476 |
| 2005/0171592 A1 | 8/2005 | Majercak | 623/1.11 |
| 2005/0183733 A1 | 8/2005 | Kawano et al. | 128/899 |
| 2005/0206774 A1 | 9/2005 | Tsujimoto | 348/345 |
| 2005/0215854 A1 | 9/2005 | Ozaki et al. | 600/109 |
| 2005/0215911 A1 | 9/2005 | Alfano et al. | 600/476 |
| 2005/0228290 A1 | 10/2005 | Borovsky et al. | 600/466 |
| 2005/0250983 A1 | 11/2005 | Tremaglio et al. | 600/101 |
| 2005/0272975 A1 | 12/2005 | McWeeney et al. | 600/113 |
| 2006/0015126 A1 | 1/2006 | Sher | 606/159 |
| 2006/0030753 A1 | 2/2006 | Boutillette et al. | 600/146 |
| 2006/0052662 A1 | 3/2006 | Kress | 600/123 |
| 2006/0100480 A1 | 5/2006 | Ewers et al. | 600/114 |
| 2006/0126064 A1 | 6/2006 | Bambot et al. | 356/337 |
| 2006/0149134 A1 | 7/2006 | Soper et al. | 600/182 |
| 2006/0149163 A1 | 7/2006 | Hibner et al. | 600/566 |
| 2006/0187467 A1 | 8/2006 | Srinivasan et al. | 356/479 |
| 2006/0202115 A1 | 9/2006 | Lizotte et al. | 250/234 |
| 2006/0252993 A1 | 11/2006 | Freed et al. | 600/146 |
| 2007/0038119 A1 | 2/2007 | Chen et al. | 600/476 |
| 2007/0066983 A1 | 3/2007 | Maschke | 606/159 |
| 2007/0088219 A1 | 4/2007 | Xie et al. | 600/473 |
| 2007/0093703 A1 | 4/2007 | Sievert et al. | 600/343 |
| 2007/0129601 A1 | 6/2007 | Johnston et al. | 600/109 |
| 2007/0213618 A1 | 9/2007 | Li et al. | 600/476 |
| 2007/0270650 A1 | 11/2007 | Eno et al. | 600/145 |
| 2008/0004491 A1 | 1/2008 | Karasawa | 600/101 |
| 2008/0221388 A1 | 9/2008 | Seibel et al. | 600/109 |

FOREIGN PATENT DOCUMENTS

| | | |
|---|---|---|
| EP | 0 520 388 | 9/1996 |
| EP | 1 077 360 | 2/2001 |
| EP | 1 088 515 | 4/2001 |
| EP | 1 142 529 | 10/2001 |
| EP | 0 712 032 | 12/2001 |
| EP | 1 310 206 | 5/2003 |
| EP | 1 421 913 | 5/2004 |
| EP | 0 910 284 | 1/2007 |
| EP | 1 063 921 | 2/2007 |
| JP | 05-154154 | 6/1993 |
| JP | 06-511312 | 12/1994 |
| JP | 2001-147398 A | 5/2001 |
| JP | 2001174744 | 6/2001 |
| JP | 2004-361889 A | 12/2004 |
| WO | WO 93/20742 | 10/1993 |
| WO | WO 96/02184 | 2/1996 |
| WO | WO 98/38907 | 9/1998 |
| WO | WO 98/43530 | 10/1998 |
| WO | WO 99/04301 | 1/1999 |
| WO | WO 01/97902 | 12/2001 |
| WO | WO 2004/068218 A2 | 8/2004 |
| WO | WO 2005/024496 | 3/2005 |

OTHER PUBLICATIONS

Barnard et al., "Single-mode Fiber Microlens with Controllable Spot Size." *Appl. Opt.* vol. 30, No. 15: 1958-1962, May 20, 1991.

Bird et al., "Two-photon fluorescence endoscopy with a micro-optic scanning head." *Optics Letters*, vol. 28, No. 17: 1552-1554, 2003.

Borreman et al., "Fabrication of Polymeric Multimode Waveguides and Devices in SU-8 Photoresist Using Selective Polymerization." *Proceedings Symposium IEEE/LEOS Benelux Chapter*, Amsterdam: pp. 83-86, 2002.

Brown et al., "Recognising Panoramas." *Proceedings of the Ninth IEEE International Conference on Computer Vision* 8pp., Apr. 2003.

Brunetaud et al., "Lasers in Digestive Endoscopy." *Journal of Biomedical Optics* vol. 2, No. 1: 42-52, Jan. 1997.

Chen et al., "Dispersion management up to the third order for real-time optical coherence tomography involving a phase or frequency modulator." *Optics Express* vol. 12, No. 24: 5968-5978, 2004.

Chen et al., "Optical Doppler tomographic imaging of fluid flow velocity in highly scattering media." *Optics Letters*, vol. 22, No. 1: 64-66, 1997.

Clark et al., "Fiber delivery of femtosecond pulses from a Ti:sapphire laser." *Optics Letters*, vol. 26, No. 17: 1320-1322, 2001.

Deschamps et al., "Automatic construction of minimal paths in 3D images: An application to virtual endoscopy." *CARS'99*—H.U. Lemke, M.W. Vannier, K. Inamura & A.G. Fannan (Editors) Elsevier Science B.V.: 151-155, 1999.

Dickensheets et al., "A Scanned Optical Fiber Confocal Microscope." *Three-Dimensional Microscopy* SPIE vol. 2184: 39-47, 1994.

Dickensheets et al., "Micromachined scanning confocal optical microscope." *Optics Letters*, vol. 21, No. 10: 764-766, May 15, 1996.

Drexler et al., "In vivo ultrahigh-resolution optical coherence tomography." *Optics Letters*, vol. 24, No. 17: 1221-1223, 1999.

Finci et al., "Tandem balloon catheter for coronary angioplasty." *Catheter Cardiovascular Diagnosis* vol. 12, No. 6: 421-425, 1986. 2pp Abstract.

Flusberg et al., "In vivo brain imaging using a portable 3.9 gram two-photon fluorescence microendoscope." *Optics Letters*, vol. 30, No. 17: 2272-2274. 2005.

Göbel et al., "Miniaturized two-photon microscope based on a flexible coherent fiber bundle and a gradient-index lens objective." *Optics Letters*, vol. 29, No. 21: 2521-2523, 2004.

Herline et al., "Surface Registration for Use in Interactive, Image-Guided Liver Surgery." *Computer Aided Surgery*, vol. 5: 11-17, 1999.

Higgins et al., "Integrated Bronchoscopic Video Tracking and 3D CT Registration for Virtual Bronchoscopy." *Medical Imaging 2003*, vol. 5031: 80-89, 2003.

Huang et al., "Optical Coherence Tomography." *Science* vol. 254, Issue 5035: 1178-1181, 1991.

Huber et al., "Amplified, frequency swept lasers for frequency domain reflectometry and OCT imaging: design and scaling principles." *Optics Express* vol. 13, No. 9: 3513-3528, May 2, 2005.

Jung et al., "Multiphoton endoscopy." *Optics Letters*, vol. 28, No. 11: 902-904, 2003.

Kiesslich et al., "Diagnosing *Helicobacter pylori* In Vivo by Confocal Laser Endoscopy." *Gastroenterology* vol. 128: 2119-2123, 2005.

Kiraly et al., "Three-Dimensional Path Planning for Virtual Bronchoscopy." *IEEE Transactions on Medical Imaging*, vol. 23, No. 9: 1365-1379, Sep. 2004.

Lee et al., "Microlenses on the End of Single-mode Optical Fibers for Laser Applications." *Appl. Opt.* vol. 24, No. 19: 3134-3139, Oct. 1, 1985.

Lexer et al., "Dynamic coherent focus OCT with depth-independent transversal resolution." *Journal of Modern Optics* vol. 46, No. 3: 541-553, 1999.

Li et al., "Optical Coherence Tomography: Advanced Technology for the Endoscopic Imaging of Barrett's Esophagus" *Endoscopy*, vol. 32, No. 12: 921-930, 2000.

Liu et al., "3D Navigation for Endoscope by Magnetic Field." *Proceedings of SPIE*, vol. 4556 25-28, 2001.

Liu et al., "Rapid-scanning forward-imaging miniature endoscope for real-time optical coherence tomography." *Optics Letters*, vol. 29, No. 15: 1763-1765, 2004.

Martinez, O.E., "3000 Times Grating Compressor with Positive Group-Velocity Dispersion —Application to Fiber Compensation in 1.3-1.6 μm Region." *IEEE Journal of Quantum Electronics* vol. 23: 59-64, 1987.

Mori et al., "A Method for Tracking camera motion of real endoscope by using virtual endoscopy system." *Proceedings of SPIE*: 1-12, 2000. <www.http://www.toriwaki.nuie.nagoya-u.ac.jp> 12pp 1-12.

Morofke et al., "Wide dynamic range detection of bidirectional flow in Doppler optical coherence tomography using a two-dimensional Kasai estimator." *Optics Letters*, vol. 32, No. 3: 253-255, Feb. 1, 2007.

Myaing et al., "Enhanced two-photon biosensing with double-clad photonic crystal fibers," *Optics Letters*, vol. 28, No. 14: 1224-1226, 2003.

Ohmi et al., "Quasi In-Focus Optical Coherence Tomography." *Japanese Journal of Applied Physics* vol. 43, No. 2: 845-849, 2004.

Oikawa et al., "Intra-operative Guidance with Real-time Information of Open MRI and Manipulators Using Coordinate-Integration Module." *Proceedings of SPIE*, vol. 5029: 653-660, 2003.

Pagoulatos et al., "Image-based Registration of Ultrasound and Magnetic Resonance Images: A Preliminary Study." *Proceedings of SPIE*, vol. 3976: 156-164, 2000.

Patterson et al., "Applications of time-resolved light scattering measurements to photodynamic therapy dosimetry." *SPIE* vol. 1203, Photodynamic Therapy: Mechanism II: 62-75, 1990.

Pyhtila et al., "Determing nuclear morphology using an improved angle-resolved low coherence interferometry system." *Optics Express*, vol. 11, No. 25: 3473-3484, Dec. 15, 2003.

Pyhtila et al., "Fourier-domain angle-resolved low coherence interferometry through an endoscopic fiber bundle for light-scattering spectroscopy." *Optics Letters*, vol. 31, No. 6: 772-774, Dec. 1, 2005.

Pyhtila et al., "Rapid, depth-resolved light scattering measurements using Fourier domain, angle-resolved low coherence interferometry." *Optical Society of America*: 6pp, 2004.

Podoleanu et al., "Three dimensional OCT images from retina and skin." *Optics Express* vol. 7, No. 9: 292-298, 2000.

Qi et al., "Dynamic focus control in high-speed optical coherence tomography based on a microelectromechanical mirror." *Optics Communications* vol. 232: 123-128, 2004.

Russo et al., "Lens-ended Fibers for Medical Applications: A New Fabrication Technique." *Appl. Opt.* vol. 23, No. 19: 3277-3283, Oct. 1, 1984.

Sasaki et al., "Scanning Near-Field Optical Microscope using Cantilever Integrated with Light Emitting Diode, Waveguide, Aperture, and Photodiode." Optical MEMS 2000 Invited Speakers: Advance Program, Sponsored by IEEE Lasers and Electro-Optics Society: 16pp, 2000. Available at <http://www.ieee.org/organizations/society/leos/LEOSCONF/MEMS/omspeak.html.>.

Schmitt et al., "An optical coherence microscope with enhanced resolving power in thick tissue." *Optics Communications* 142: 203-207, 1997.

Schwartz et al., "Electromagnetic Navigation during Flexible Bronchoscopy." *Interventional Pulmonology: Respiration*, vol. 70: 516-522, 2003.

Seibel et al., "Unique Features of Optical Scanning, Single Fiber Endoscopy." *Lasers in Surgery and Medicine* vol. 30: 177-183, 2002.

Shahidi et al., "Implementation, Calibration and Accuracy Testing of an Image-Enhanced Endoscopy System." *IEEE Transactions On Medical Imaging*, vol. 21, No. 12: 1524-1535, 2002.

Shinagawa et al., "CT-Guided Transbronchial Biopsy Using an Ultrathin Bronchoscopic Navigation." *Chest*, vol. 125, No. 3: 1138-1143, 2003.

Shiraishi et al., "Spot Size Reducer for Standard Single-Mode Fibers Utilizing a Graded-Index Fiber Tip." *ECOC 97*: 50-53, Sep. 22-25, 1997.

Shoji et al., "Camera motion tracking of real endoscope by using virtual endoscopy system and texture information." *Proceedings of SPIE*, vol. 4321: 122-133, 2001.

Skala et al., "Multiphoton Microscopy of Endogenous Fluorescence Differentiates Normal, Precancerous, and Cancerous Squamous Epithelial Tissues." *Cancer Research* vol. 65, No. 4: 1180-1186, Feb. 15, 2005. Available at <www.aacrjournals.org>.

Solomon et al., "Three-dimensional CT-Guided Bronchoscopy With a Real-Time Electromagnetic Position Sensor," "A Comparison of Two Image Registration Methods." *Chest*, vol. 118, No. 6: 1783-1787, 2000.

Srivastava, S., "Computer-Aided Identification of Ovarian Cancer in Confocal Microendoscope Images," Department of Electrical and Computer Engineering, University of Arizona Graduate School, Thesis: 213pp, 2004.

Tearney et al., "Determination of the Refractive-Index of Highly Scattering Human Tissue by Optical Coherence Tomography." *Optics Letters*, vol. 20, No. 21: 2258-2260, 1995.

Tsai et al., "All-Optical Histology Using Ultrashort Laser Pulses." *Neuron* Cell Press, vol. 39: 27-41, Jul. 3, 2003.

Vakoc et al., "Comprehensive esophageal microscopy by using optical frequency-domain imaging (with video)." *Gastrointestinal Endoscopy*, vol. 65, No. 6: 898-905, 2007.

Wang et al., "Deep Reactive Ion Etching of Silicon Using An Aluminum Etching Mask." *Proceedings of SPIE*, vol. 4876: 633-640, 2003.

Wilson et al., "Optical Reflectance and Transmittance of Tissues: Principles and Applications." *IEEE Journal of Quantum Electronics*, vol. 26, No. 12: 2186-2199, Dec. 1990.

Xu et al., "3D Motion Tracking of pulmonary lesions using CT fluoroscopy images for robotically assisted lung biopsy." *Proceedings of SPIE*, vol. 5367: 394-402, 2004.

Yamada et al., "Characteristics of a Hemispherical Microlens for Coupling Between a Semiconductor Laser and Single-Mode Fiber." *IEEE J. Quant. Electron*, vol. QE-16, No. 10: 1067-1072, Oct. 1980.

Yamamoto et al., "Total enteroscopy with a nonsurgical steerable double-balloon method." *Gastrointestinal Endoscopy* vol. 53, No. 2: 216-220, Feb. 2001. Abstract only.

Yang et al., "High speed, wide velocity dynamic range Doppler optical coherence tomography (Part I): System design, signal processing, and performance." *Optics Express*, vol. 11, No. 7: 794-809, Apr. 7, 2003.

Yang et al., "Micromachined array tip for multifocus fiber-based optical coherence tomography." *Optics Letters*, vol. 29, No. 15: 1754-1756, 2004.

Yelin et al., "Three-dimensional miniature endoscopy." *Nature* vol. 443: 765 plus supplemental information, Oct. 19, 2006. <www.nature.com/nature/journal/v443/n7113/extref/443765a-s2.doc>.

Yoon et al., "Analysis of Electro Active Polymer Bending: A Component in a Low Cost Ultrathin Scanning Endoscope." *Sensors and Actuators A—Physical*: pp. 1-26, Submitted Jan. 13, 2006, Published Jul. 2006.

Yun et al., "Comprehensive volumetric optical microscopy in vivo." *Nature Medicine* vol. 12, No. 12: 1429-1433, Dec. 2006.

Yun et al., "Motion artifacts in optical coherence tomography with frequency-domain ranging." *Optics Express* vol. 12, No. 13: 2977-2998, Jun. 28, 2004.

Zhang et al., "In vivo blood flow imaging by a swept laser source based Fourier domain optical Doppler tomography." *Optics Express* vol. 13, No. 19: 7449-7457, Sep. 19, 2005.

Zipfel et al., "Live tissue intrinsic emission microscopy using multiphoton-excited native fluorescence and second harmonic generation." *PNAS* vol. 100, No. 12: 7075-7080, Jun. 10, 2003. Available at <www.pnas.org/cgi/doi/10.1073/pnas.0832308100>.

n.a., "Given® Diagnostic System." The Platform for PillCam™ Endoscopy Given Imaging Ltd.: 4pp, 2001-2004. <http:www.givenimaging.com>.

n.a., "NASA-Inspired Shape-Sensing Fibers Enable Minimally Invasive Surgery." NASA Tech Briefs vol. 32, No. 2: 12, 14, Feb. 2008.

n.a., "NANO™ SU-8 2000 Negative Tone Photoresist Formulations 2002-2025." Micro-Chem: 5pp, © 2001.

Barhoum, Erek S., Richard S. Johnston, and Eric J. Seibel. "Optical modeling of an ultrathin scanning fiber endoscope, a preliminary study of confocal versus non-confocal detection," Optics Express vol. 13, No. 19, Sep. 19, 2005. pp. 7548-7562.

Fu, Ling, Xiaosong Gan, and Min Gu. "A Nonlinear Optical Microscope by Use of Double-clad Photonic Crystal Fibers," © 2005 Optical Society of America.

Helmchen, Fritjof, Michale S. Fee, David W. Tank, and Winfried Denk. "A Miniature Head-Mounted Two-Photon Microscope: High Resolution Brain Imaging in Freely Moving Animals," Neuron, vol. 31, Septebmer 27, 2001, pp. 903-912.

Lewis, John R., Mark Holton, Martin Kykta, Amjad Malik, Frank Metting, Chris Ryerson, Chris Wiklof, Jianhua Xu. "Scanned beam medical imager," MOEMS Display and Imaging System II, edited by Hakan Urey, David L. Dickensheets, Proceedings of SPIE vol. 5348, Bellingham, WA 2004, pp. 40-51.

Murakami, Kenzi, Akiko Murata, Takeshi Suga, Hideya Kitagawa, Yoshitaka Kamiya, Mitsunori Kubo, Kazuya Matsumoto, Hiroshi Miyajima, and Masahiro Katashiro. "A Miniature Confocal Optical Microscope With Mems Gimbal Scanner," The $12^{th}$ International Conference on Solid State Sensors, Actuators and Microsystems, Boston, Jun. 8-12, 2003, pp. 587-590.

Smithwick, Quinn Y.J., Juris Vagners, Per G. Reinhall, Eric J. Seibel. "Modeling and Control of the Resonant Fiber Scanner for Laser Scanning Display or Acquisition," SID 03 Digest, pp. 1455-1457.

Yelin, D., B.E. Bouma, S.H. Yun, and G.J. Tearney. "Double-clad fiber for endoscopy," Optics Letters vol. 29, No. 20, Oct. 15, 2004. pp. 2408-2410.

European search report and opinion dated Apr. 4, 2011 for EP Application No. 05852111.3.

* cited by examiner

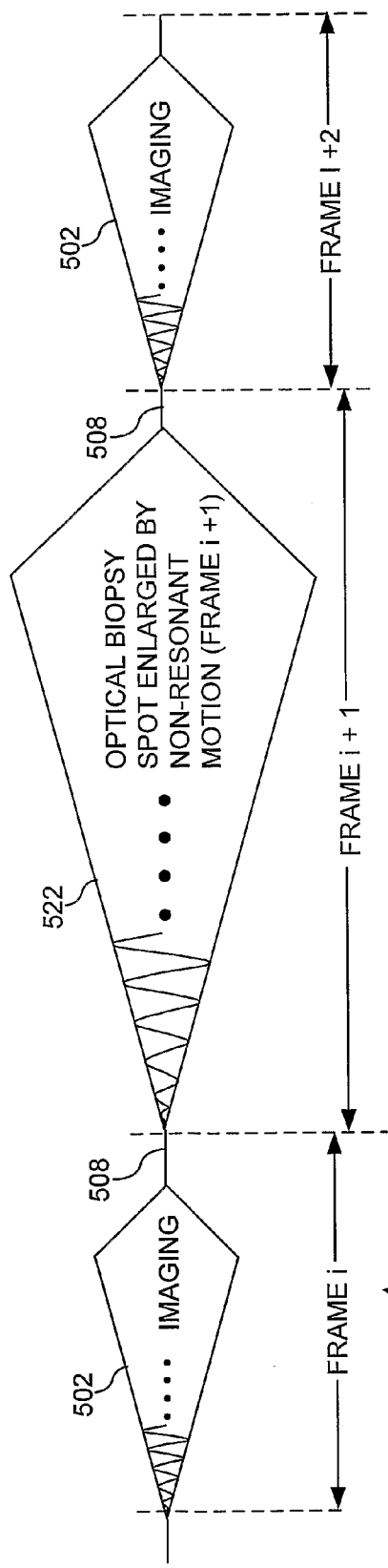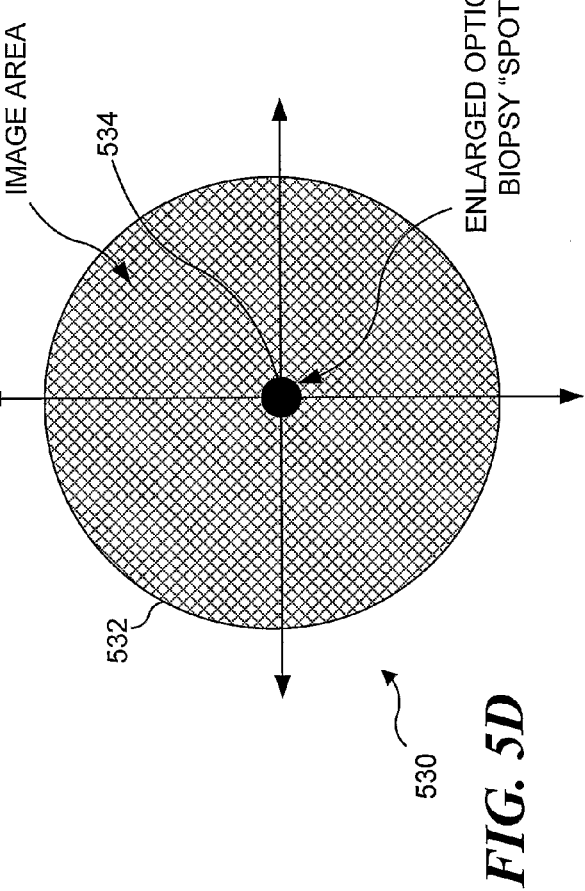
FIG. 5C
FIG. 5D

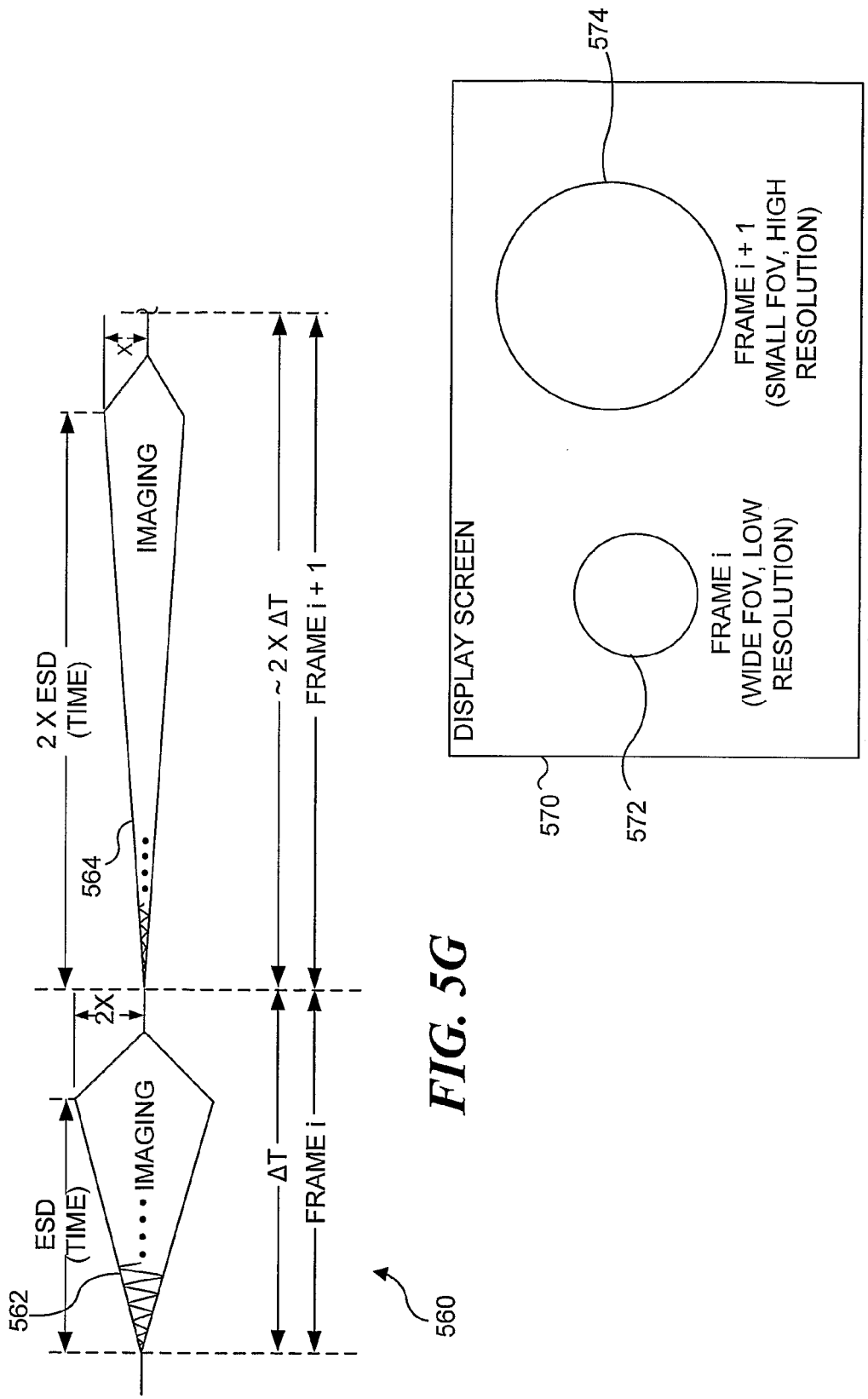

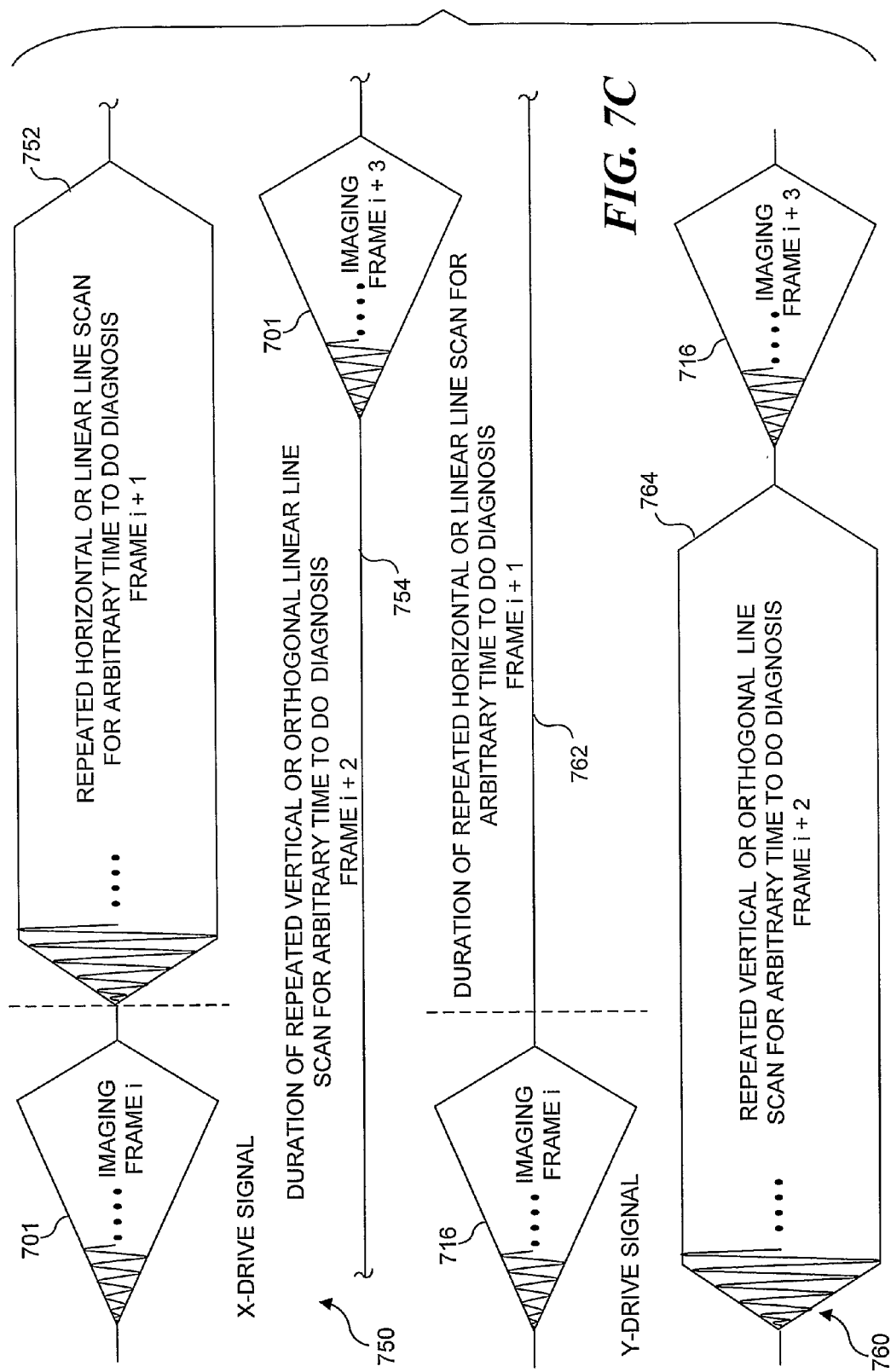

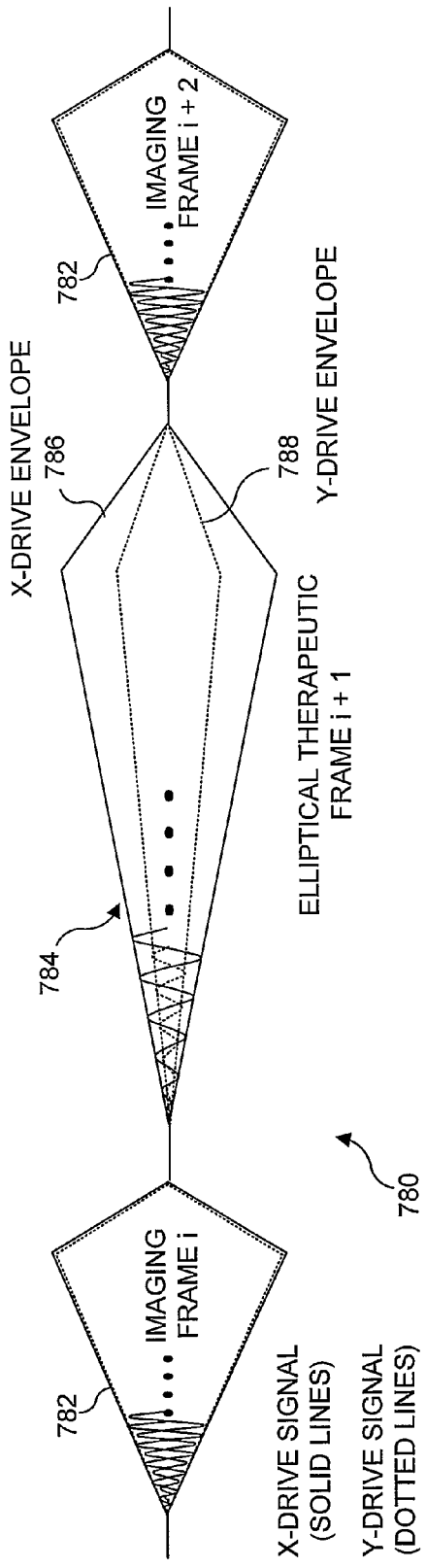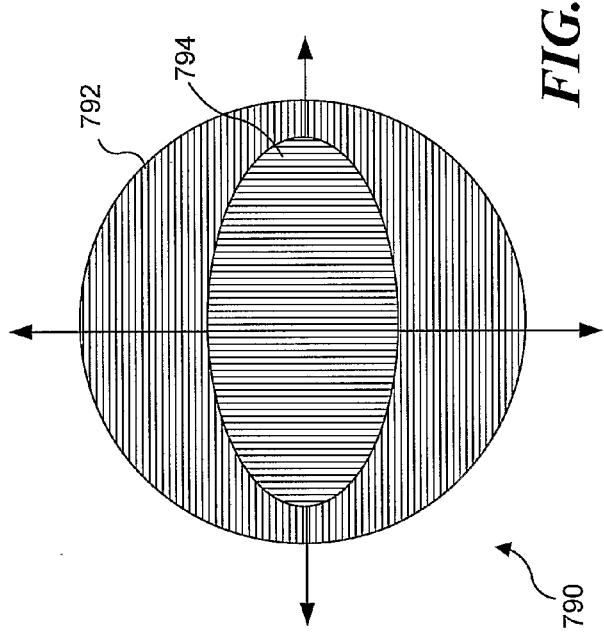
*FIG. 7E*
*FIG. 7F*

SCANNING BEAM WITH VARIABLE SEQUENTIAL FRAMING USING INTERRUPTED SCANNING RESONANCE

GOVERNMENT RIGHTS

This invention was made with U.S. Government support under grant Nos. CA094303, R21 CA110184, CA094303-R33, and CA110184-R21 awarded by the National Institute of Health. The U.S. Government has certain rights in the invention.

BACKGROUND

The burgeoning field of minimally invasive medical procedures (MIMPs) has increased the demand for systems that produce less tissue damage and trauma, faster recovery times, and lower risks to the patient. Ideally, the practitioner of MIMPs requires smaller instruments that perform a greater variety of functions. Furthermore, a "one-instrument-does-all" approach must add simplicity, not complexity, by ensuring that it is easy to use, minimizing the time required to master its operation.

The instruments used by practitioners of MIMPs typically include several different discrete systems for optical imaging, monitoring, maneuvering, sizing, diagnosis, biopsy, therapy, surgery, and non-visual monitoring/sensing. It clearly is preferable to combine the functions provided by these instruments in a single compact device to reduce the number of surgical ports that are currently required for a plurality of single-function tools, each providing only a single one of these functions. By employing an integrated multi-functional tool so that only one small port is used, the risks associated with repeatedly removing and inserting surgical tools can be dramatically reduced. Since most MIMPs require the practitioner to constantly monitor the procedure visually, optical imaging to identify a specific site to next render therapy or to view the results of the therapy already rendered is considered a requirement for any fully integrated system for MIMPs. Thus, an appropriate multifunction instrument will most likely include an optical imaging system, and the imaging system should be integrated with one or more diagnostic, imaging, and/or therapeutic tools.

At present, the tools commonly used for MIMPs cannot readily be integrated into a single device without increasing the size of the resultant instrument to an excessive degree. For example, all commercial optical imaging systems that include a maneuverable flexible shaft must maintain a certain size (diameter) in order to preserve image quality. Currently, flexible scopes cannot be made smaller than this limit unless image field of view (FOV) or resolution is sacrificed. Although imaging and some diagnostic capability can be integrated into existing scopes now in use, such as standard tissue imaging in combination with fluorescence for early detection of cancers, the optical systems of current flexible scopes cannot provide integrated diagnoses and therapies at the required degrees of performance, size, and price that will be demanded in the future by medical practitioners.

Current Technology Used for MIMPs

Flexible scope designs that are now commercially available use either a bundle of optical fibers (optical waveguides) and/or one or more cameras having an array of detectors to capture an image. Thus, the diameter of these flexible scopes employed for remote imaging cannot be reduced to smaller than the image size. Ignoring the optical fibers used for illumination, the scope diameter is therefore limited by the individual pixel size of a camera or by the diameter of optical fibers used to acquire the image. Currently, the smallest pixel element is determined by the size of the end of an optical fiber, which has a minimum core diameter of about 2 µm. To propagate light through an optical fiber, a surrounding cladding layer is required, increasing the minimum pixel size to more than 3 µm in diameter. If a standard VGA image is desired (e.g., with a resolution of 640×480 pixels), then a minimum diameter required for just the image optical fiber is more than 2 mm. Therefore, resolution and/or FOV must be sacrificed by having fewer pixel elements in order to achieve scopes with less than 2 mm overall diameter. All commercially available scopes suffer from this fundamental tradeoff between high image quality and small size.

Thus, it would be desirable to add diagnostic, monitoring, and therapeutic (or optical surgical) capability to a remote imaging system for the purpose of reducing the overall size of the instrument used for MIMPs. Since, for the reasons noted above, the current design for flexible scopes cannot readily be reduced in size without reducing imaging performance, the options for integrating diagnostic and therapeutic applications with an imaging system would appear to require an increase in the size of the instrument or use of separate instruments for each function. For example, a high intensity light source might be added to a general endoscopic surgical system to carry out photodynamic therapy (PDT) or laser surgery, or a polarized light source or other multi-spectral specialty light sources might be needed for diagnosis and/or sensing a condition of an ROI. However, the white light illumination for standard endoscopic imaging is typically provided through an optical fiber bundle that diffusely illuminates the tissue and is incapable of providing a directed optical energy at high intensity and resolution to produce effective optical therapies, and will often not have the characteristics required for diagnostic processes. Therefore, any optical therapies that require directed illumination of high intensity light, such as PDT and laser surgery, or any diagnostic processes that also require a special light source cannot use existing optical designs for flexible imaging scopes, but instead, must rely on a second optical pathway and separate control mechanisms.

To perform diagnostic or therapeutic MIMPs, one or more separate instruments are used within the FOV of a standard endoscopic imager, and any additional separate instrument often must be held and maneuvered by a second medical practitioner. Typically, the second instrument provides a high intensity point source of light for optical therapies, a hot-tipped probe for thermal therapies, or a trocar used for mechanical cutting. The second instrument is moved to the surface of the tissue and usually moved within or across the surface of the tissue, covering the area of interest as the tool is scanned and manipulated by hand. These secondary instruments are inserted into the patient's body through a separate port, and thus, while being used, are viewed from a different point of view in the visual image. Furthermore, the therapeutic instrument often blocks the practitioner's direct view of the ROI with the imaging tool, making highly accurate therapies quite difficult for the medical practitioner to achieve. Significant amounts of training and practice are required to overcome these difficulties, as well as the capability to work with a reduced sense of touch that is conveyed through the shaft of an instrument having friction and a non-intuitive pivot at the point of entry. Thus, to work effectively with current imaging and therapeutic technologies, the practitioner of MIMPs must be highly trained and skilled.

Clearly, there is a need for an instrument that integrates imaging, diagnostic, and therapeutic functions, delivers these functions through a relatively small diameter, and is sufficiently intuitive to use as to require little training or skill. Ideally, the instrument should be implemented using a single optical fiber, but should still be capable of providing a sufficient FOV, good image size, and resolution, and should ensure that the ROI within a patient's body while administering therapy corresponds to that during imaging. Currently, none of the instruments commercially available provide these capabilities and cannot be easily modified to provide such capabilities.

At least a partial solution to these problems has been developed, as disclosed in U.S. patent application Ser. No. 09/850, 594 (this application was allowed and the Issue fee was paid more than one year ago, but the Letters Patent has not yet been issued). This application, which is entitled, "Medical Imaging, Diagnosis, and Therapy Using a Scanning Single Optical Fiber System" and which was filed on May 7, 2001, discloses how the distal end of a single optical fiber can be driven into a resonant or near resonant motion and used for providing imaging, monitoring, sensing, screening, diagnosis, and therapy for a region of interest in a patient's body. However, a problem arises when an attempt is made to add a therapeutic high-power laser light source to the scanning fiber endoscope of this earlier disclosure, so that the same optical fiber can be used for therapy provided by the high-power laser, as well as for imaging, optical diagnosis, and optical monitoring, during a MIMP.

There are two scenarios in which the same resonant optical fiber might be used for providing this combined functionality in a single compact device. In the first scenario, a single optical fiber is coupled to red, green, and blue (RGB) lasers for imaging, and is also selectively coupled to the high-power laser for providing therapy to a site. Following the teaching of the earlier patent application, the high-power laser would be energized only briefly to illuminate a single or few pixels for a very short dwell time, which as disclosed in this application, would be the same dwell time used for low-power laser light imaging with the RGB lasers, since the motion of the resonant optical fiber is not interrupted between the imaging a site and rendering therapy to the site. In this first scenario, the same single mode optical fiber for imaging is used for delivering the high-power pulse.

However, a substantial problem with this first approach is the short dwell time that is appropriate for the color imaging of tissue is fixed, but will typically be too short for the effective delivery of optical therapy. If the fixed dwell time is too short to perform the optical therapy using the laser power that can be delivered via the same single mode optical fiber, then an alternative approach is required. This alternative might require using additional optical fibers that only deliver therapeutic optical power to the tissue, separate from the resonant optical fiber scanner that is used for imaging, diagnostic, and/or monitoring functions. In this alternative, it is most likely that the separate optical fibers used for therapy would be non-scanning, creating fixed points of therapeutic illumination within the imaging field. If the therapeutic optical fibers are fixed in place, then the dwell times of high power laser illumination can extend as long as the therapeutic laser light source is energized, assuming that the endoscope can be held stationary with the high power laser light directed where desired at the site. Unfortunately, this second alternative approach increases the size and complexity of the endoscope and will probably not offer the option to readily scan the therapeutic optical fibers over a portion of the site to which the therapy is to be rendered. Fixed therapeutic optical fibers would require that the distal end of the endoscope be maneuvered to direct the high intensity light emitted from the distal end of the therapeutic optical fibers toward the desired treatment site. It would be preferable to develop a different way to render both therapy and one or more of the other functions of imaging, diagnosis, and monitoring using only a scanning optical fiber that would enable different dwell times for any one of these functions.

It would also be desirable to change the size of a scanned pattern, as well as its shape, and other characteristics, when providing any of the desired functions using a single scanning optical fiber. For example, a scanning pattern during imaging might image a substantially larger region compared to a relatively smaller portion of that region that should be scanned when delivering therapy, or doing an optical diagnosis. None of the earlier disclosure provided any technique for interrupting a scanning optical fiber to change functional modes and to change to the scanning characteristics that are appropriate for a specific function.

Since variable sequential framing provides imaging and one of diagnosis, therapy, and monitoring in time-series by using the same resonant scanning device, it is desirable to minimize the time required for the non-imaging function that occurs in a frame-sequential manner with the imaging function. In general, for therapy and some diagnoses, a shorter dwell time will reduce the localized heating and minimize optical damage to non-targeted tissue that may be caused by laser light directed at the tissue. However, shorter dwell times require higher peak power for the laser source, putting the light conductive medium at risk for optical damage. A specially conditioned light conductive medium assists in increasing the optical damage threshold and thus enables dwell times to be minimized. Because the risk for optical damage cannot be completely mitigated, it is desirable to monitor the ends of the light conductive medium for damage, so that the practitioner can avoid using the device when the light conductive medium is not functioning properly. Should the light conductive medium sustain damage, it will be necessary for the practitioner to replace the medium with a new one to restore the system functionality. Therefore the system should include means facilitating replacement of the light conductive medium in a manner that does not require a great amount of technical proficiency in coupling a light conductive medium to a light source. This goal can be achieved by including an automated positional control system with a software-based alignment routine that is independent of input by the user.

Another technique to reduce dwell times is the use of extrinsic chromaphores in the ROI. When applied by the practitioner, these chromaphores can assist in light absorption and thus localized heating, reducing the necessary dwell time of the applied light. The practitioner may want to use specific chromaphores for individual diagnostic or therapeutic procedures. Thus, it is desirable that a diagnostic or therapeutic system include contingencies for procedures involving the most often used chromaphores and fluorophores. These contingencies will very likely involve a variation of the dwell time in order to compensate for the chromaphore.

It is often necessary to monitor the progress of applied therapy in order to determine when the procedure is complete, since the time at which completion occurs may not be known to the practitioner beforehand. Previously used approaches have provided for image collection using fixed fiber detectors; however, there are other techniques that are useful in this situation. For example, collecting infrared radiation from the ROI can give a valuable clue to the temperature of the region. Monitoring the polarization of the light returned from the ROI can be a valuable in determining the state of the target of therapy. Time-of-flight measurements can give specific information as to the depth or distance of the ROI from the distal tip of the scope. Thus, in at least one embodiment a surgical scope should have the ability to monitor the progress of applied therapy by collecting feedback from the ROI.

SUMMARY

Accordingly, a new approach has been developed for scanning a region with a beam of light during a plurality of scanning frames, which is embodied in an exemplary scanning device. The scanning device includes a light conductive medium configured to convey light from a source. A scanning element is coupled to the light conductive medium and is configured to direct light conveyed through the light conductive medium to the region by scanning the region in a desired pattern. A driver is coupled to the scanning element, to apply a force to the scanning element that causes the scanning element to move so that the light beam scans over the region in the desired pattern. Further, a control supplies a driving signal to the driver to vary at least one of an amplitude and a direction of the force applied by the driver to the scanning element. This driving signal causes the driver to move the scanning element in a first mode during one scanning frame, and in a second mode during a subsequent scanning frame. At least one characteristic of the desired pattern in the first mode is substantially different in the second mode.

In one exemplary embodiment, the driver is configured to apply the force to move the scanning element relative to two generally orthogonal directions. In at least one embodiment that is discussed below, the scanning element comprises a movably mounted light reflective surface (e.g., a mirror) that is configured to be driven into motion by the driver, so that the light beam is reflected from the light reflective surface toward the region, thereby scanning the region in the desired pattern.

While not required, in one exemplary embodiment, the force applied by the driver drives the scanning element generally into a resonant motion, to achieve the desired pattern. In this case, the resonant motion of the scanning element can be interrupted between successive scanning frames.

In one exemplary embodiment, the light conductive medium is configured to be coupled to or in communication with a first source of light during the one frame, and to a second source of light during the subsequent frame. The first source produces light that is substantially different than the light produced by the second source. For example, the light produced by the first source can substantially differ from the light produced by the second source in regard to at least one of an intensity of the light, the pulsed or continuous nature of the light, and a waveband of the light.

In one exemplary embodiment, the light conductive medium is a singlemode optical fiber that both conveys multispectral light to the scanner while also being an integral part of the scanning element. In at least one embodiment that is discussed below, a resultant point source of light from the distal tip of such a singlemode optical fiber can be scanned in two generally orthogonal directions at or near the mechanical resonance of the fiber scanner. A multidimensional scanning pattern can be generated by modulating the amplitude of the resonant motion of the scanned light to generate the desired pattern.

In another exemplary embodiment, at least one end of a small-core optical fiber has been conditioned to allow the propagation of higher intensities of light without damage. Forms of conditioning may include, for example, an end cap, an aperture, a mechanical polish, an optical polish, and/or a hermetic seal. The proximal end of the optical fiber that conducts the imaging and therapy can be monitored to detect damage using, for example, video imaging, or light reflectance measurement.

The at least one characteristic of the desired pattern that is different in the first mode than in the second mode can be a scan pattern size, shape, depth, duration, resolution, or a quality of the light comprising the light beam. The control can also be configured to selectively control a dwell time for scanning the light beam over the region, so that a substantially different dwell time is employed during the first mode than during the second mode.

The scanning device may also include a light detector that receives light from the region. The light detector is preferably configured to connect to a display for displaying an image of the region. Accordingly, the first mode can be used for at least one of imaging the region, monitoring a state of the region, providing a therapy with the light beam to the region, and diagnosing a condition of the region. Similarly, the second mode can be used for at least one of imaging the region, monitoring a state of the region, providing a therapy with the light beam to the region, and diagnosing a condition of the region.

Depending, for example, on the application of the scanning device, the desired pattern in each of the first mode and the second mode can include, for example, at least one of a generally circular scan, a generally elliptical scan, a point scan (i.e., if the scanning element is not being moved), a linear scan, a propeller scan, and a Lissajous scan.

Another aspect is directed to a method for scanning a light beam over a region to achieve a plurality of different functions during subsequent scanning frames. The steps of this method are generally consistent to the functions provided by the scanning device, as noted above.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein.

Figure 2A:
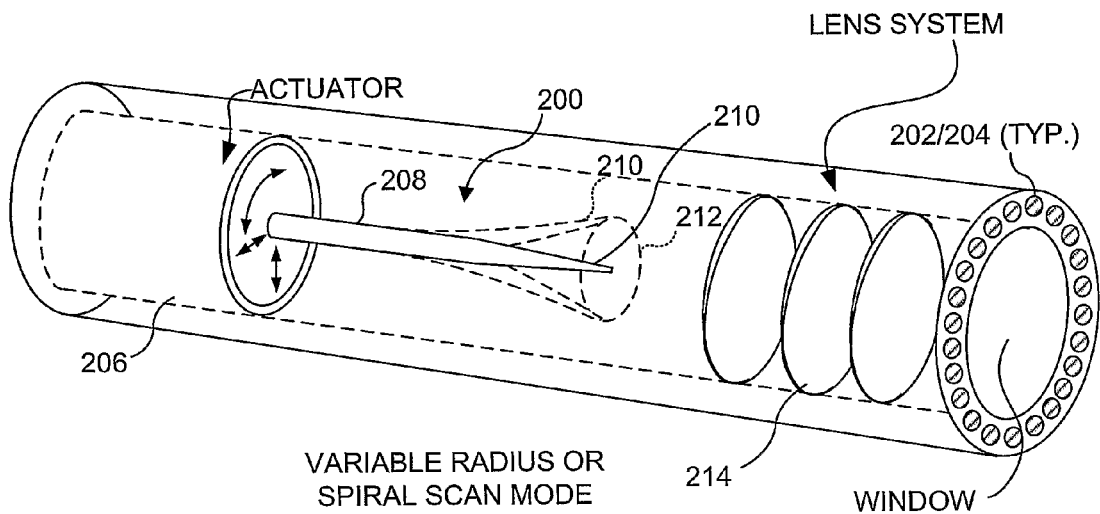
FIG. 2A illustrates an exemplary scanning device having a tapered optical fiber that can be driven to scan a region in a variable radius circular, or spiral scanning mode.
Figure 2B:
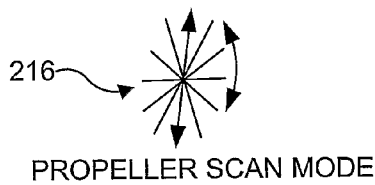
Figure 2C:
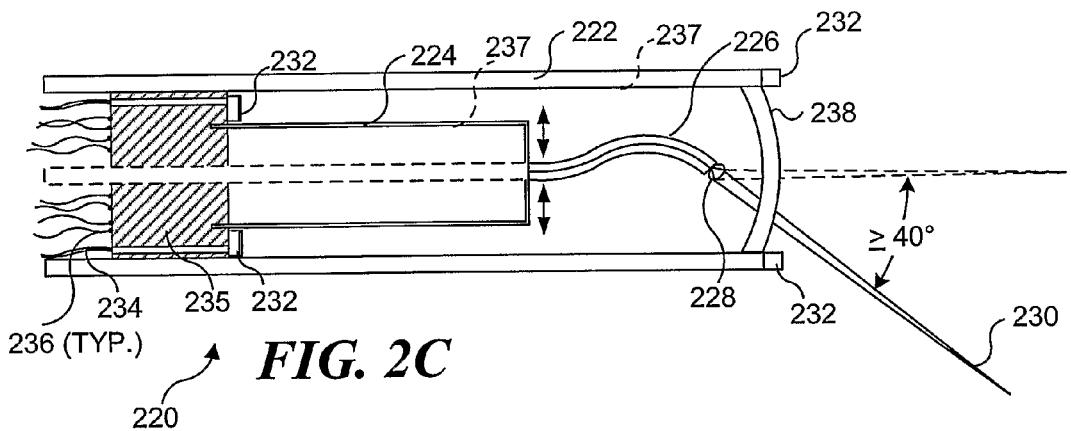
Figure 3:
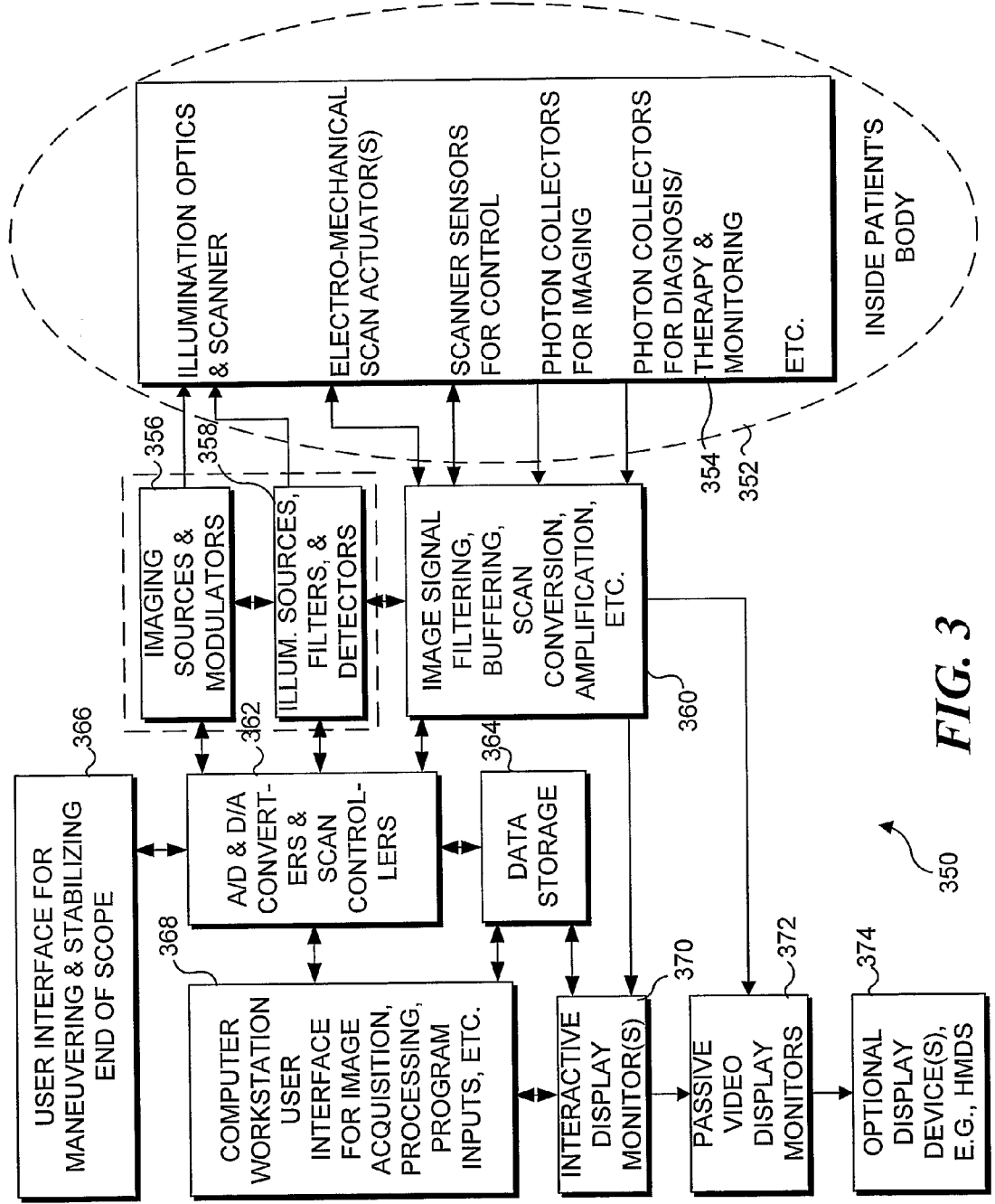
Figure 4:
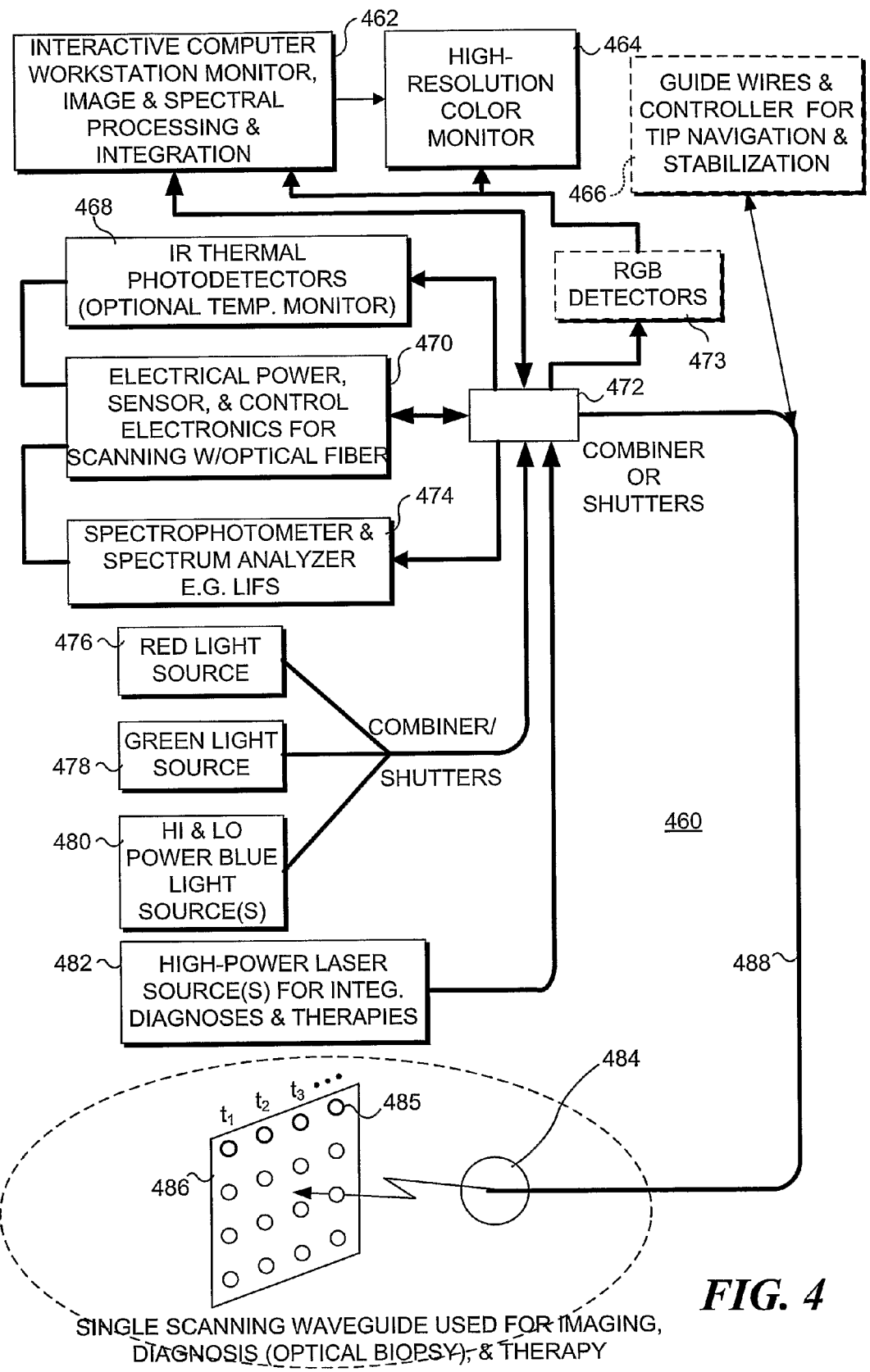
Figure 8:
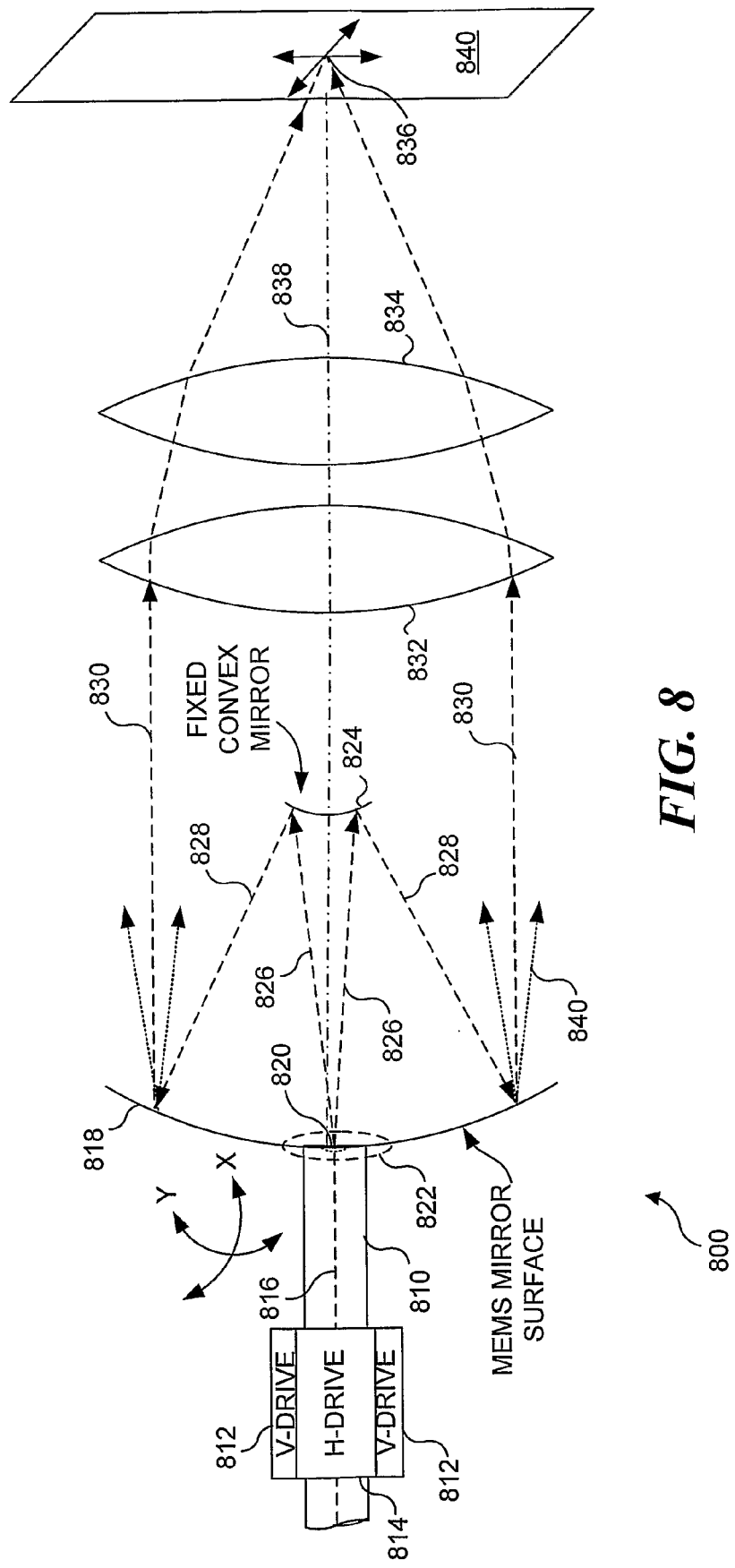
Figure 9:
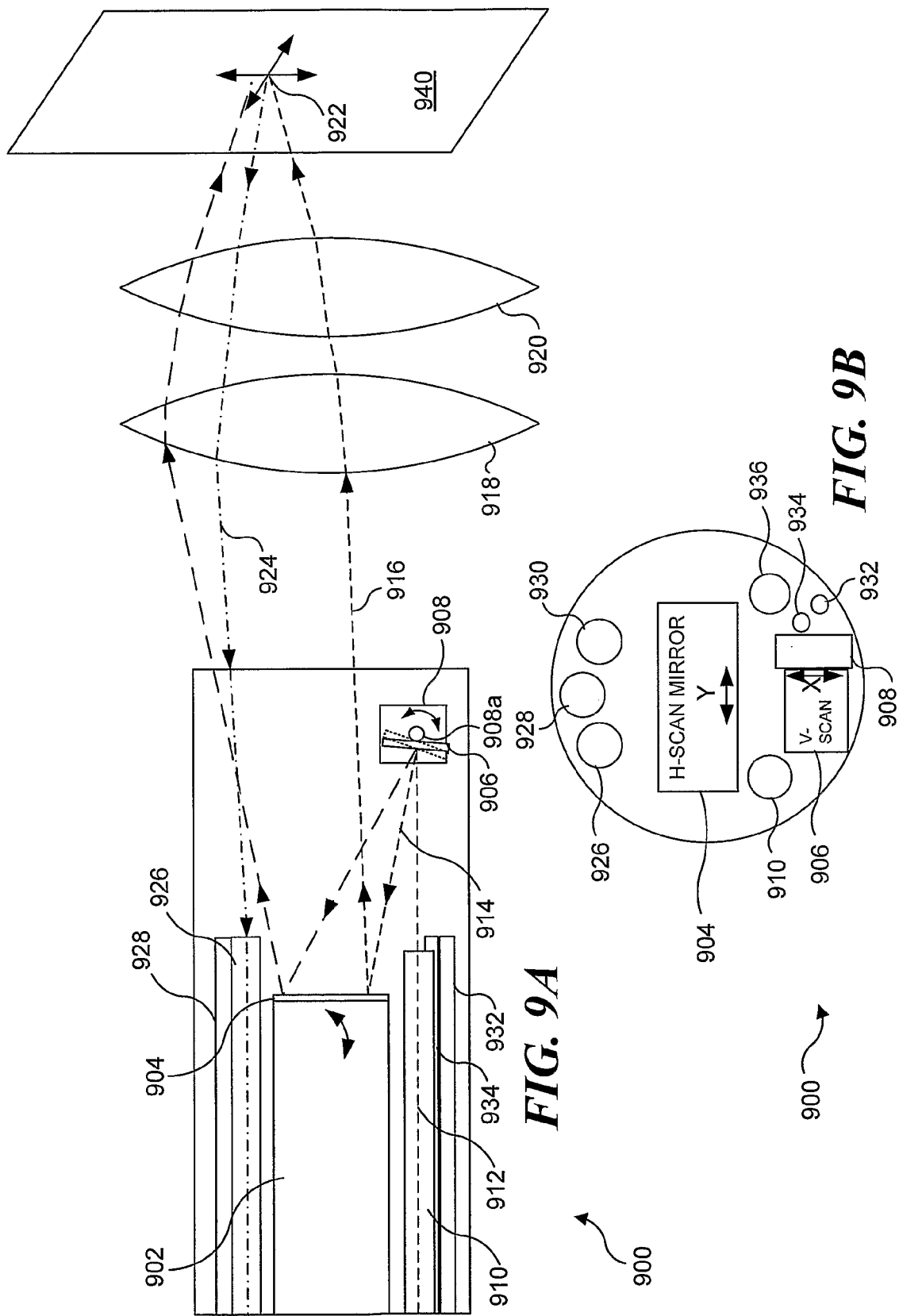

FIG. 2B schematically illustrates an exemplary propeller scan mode in which an optical fiber can be driven;

FIG. 2C is a schematic diagram showing a scanning device having an optical fiber that is fitted with a microlens and is configured to be driven into a mechanical resonance to scan a region;

FIG. 3 is a block diagram illustrating the functional flow of signals in a system that is usable with a scanning device as described herein, for imaging, monitoring, rendering diagnoses, and for providing therapy to a region FIG. 4 is a functional block diagram of an integrated cancer imaging, screening, and biopsy scanning system, with both optical therapy delivery and monitoring capabilities;

FIGS. 5A-5H are exemplary graphic views illustrating different exemplary scanning X-drive signals to a resonant fiber scanner and the resulting two-dimensional scanning patterns, wherein an interruption occurs between successive scanning frames for the purpose of imaging and diagnosis;

FIGS. 6A-6D are exemplary graphic views illustrating different exemplary scanning X-drive signals to a resonant fiber scanner and the resulting two-dimensional scanning patterns, wherein an interruption occurs between successive scanning frames for the purpose of diagnosis, therapy, and monitoring;

FIGS. 7A-7F are graphic illustrations of an exemplary X drive signal and an exemplary Y drive signal to a resonant fiber scanner and the resulting non-circular two-dimensional scanning patterns, wherein an interruption occurs between successive frames for the purpose of diagnosis and therapy;

FIG. 8 is a schematic side view of an embodiment that employs a moving mirror surface and a fixed mirror, to scan a region; and FIGS. 9A and 9B are respectively a schematic side view and an end view of an embodiment that includes two moving mirrors to scan a region.

Figure 10:
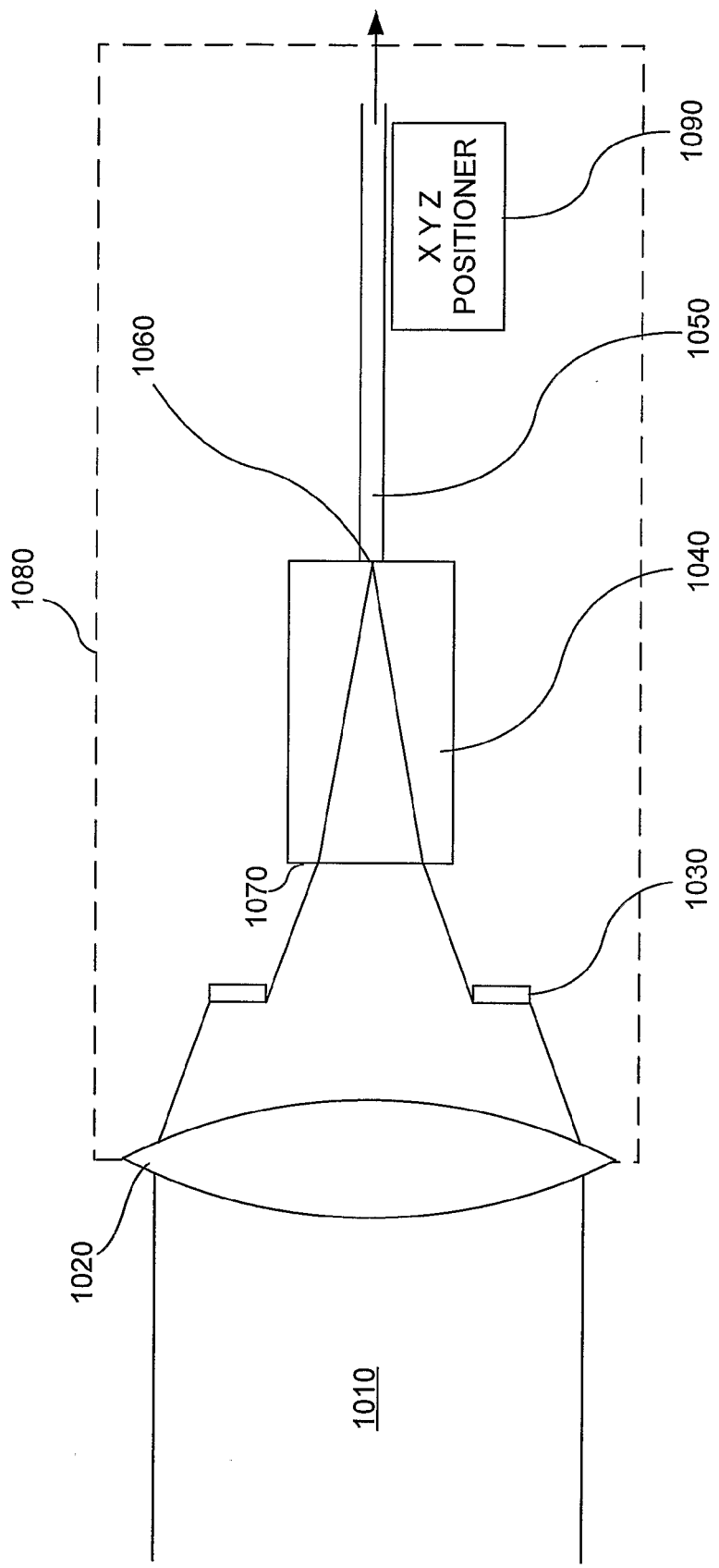

FIG. 10 illustrates an exemplary light conducting medium as a small-core optical fiber that has been conditioned to increase the optical damage threshold.

DESCRIPTION

Figures and Disclosed Embodiments Are Not Limiting

Exemplary embodiments are illustrated in referenced Figures of the drawings. It is intended that the embodiments and Figures disclosed herein are to be considered illustrative rather than restrictive.

Exemplary Scanning Device

The technique discussed below for driving a scanning device, so that successive scanning frames provided by the scanning device differ in regard to at least one characteristic such as scanning frequency, scanning pattern, amplitude, duration, etc. is applicable to a variety of different types of scanning devices and in regard to a number of different applications. The term "scanning frame" has a clearly evident meaning when used in connection with acquiring a single image frame by scanning a site. However, as used herein, "scanning frame" (or simply, "frame") is intended to mean an interval of time in which a scanning device operates in a specific mode, e.g., moves in a specific pattern or with a specific amplitude or frequency. The frame is typically repeated continuously during normal imaging-only operation.

Figure 1A:
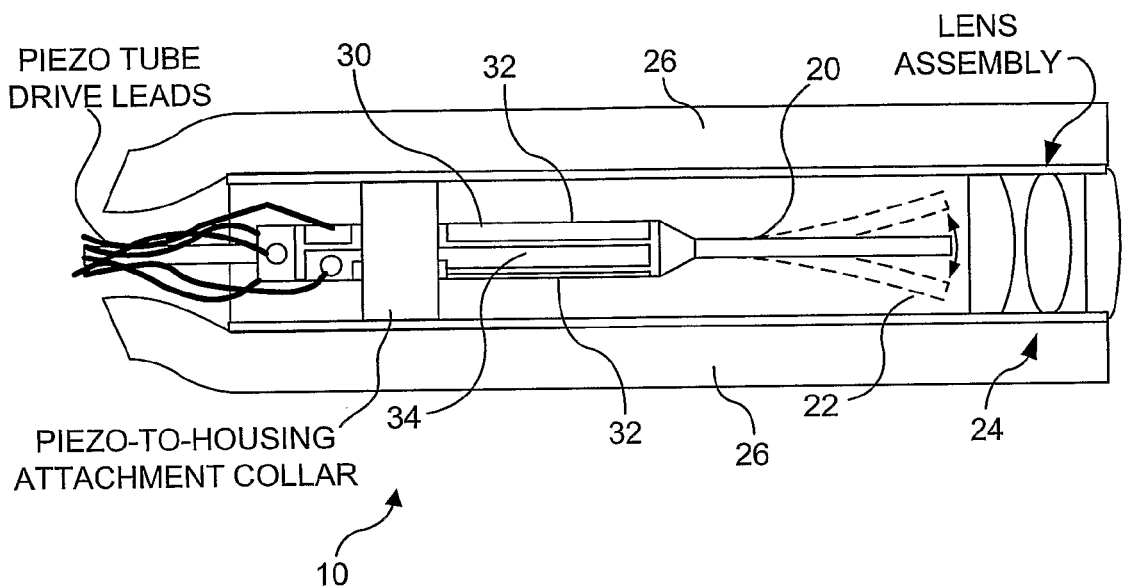
FIG. 1A illustrates an exemplary scanning device having a singlemode optical fiber that can be driven to scan a region in a amplitude-modulated resonant pattern comprising a line or a variable radii ellipse.

The best embodiment due to its simplicity is illustrated in FIG. 1A, which shows an optical fiber device 10, which is drivable in a variable linear or elliptical scan mode. The scan mode shown in this figure can be generated by driving an optical cantilever 20, into a resonant (or near resonant) condition using, for example, a piezoceramic tube actuator 30. A single-axis (linear) scan pattern 22 can be generated by applying voltage on one or opposing electrodes of an actuator 32. By applying an oscillating voltage (e.g., a sine wave) at or near the mechanical resonant frequency of the base-excited fiber cantilever, the amplitude of the tip motion can be mechanically amplified due to the mechanical resonance of the fiber cantilever. For example, the concurrent application of a second sinusoidal voltage (cosine wave) to the second orthogonal set of electrodes 34 on the actuator, at the same or slightly different resonant frequency, causes the resonating fiber tip to move in an elliptical pattern.

An image is generated by the fiber scanner shown in FIG. 1A by focusing the light from the scanned distal tip of the fiber using imaging lenses 24. Typically the imaging lenses focus and magnify the scanned point source from the scanning fiber tip to the region of interest (ROI) in either the linear (one-dimensional) or elliptical (two-dimensional) patterns. By varying the amplitude of the voltages applied to the actuator during the elliptical scan, a two-dimensional (2-D) space-filling illumination pattern is formed. Light collection optical fibers 26 that surround the fiber scanner are used to collect the backscattered illumination light that provides the signal for generating the 2-D image in time series (one pixel at a time). Typically light collection optical fibers 26, are large-core and high numerical aperture, multimode optical fibers for the purpose of increasing light collection efficiency. In contrast, optical fiber 20, which is used for the scanned illumination, is a singlemode optical fiber. A singlemode optical fiber provides the smallest effective point source that reduces the point spread function (PSF) of the scanned spot on the region of interest, enabling the highest spatial resolution from the 2-D image. The singlemode fiber can be the small-core optical fiber commonly used in telecommunication and sensing applications or photonic crystal or bandgap optical fibers that are microstructured fibers and which can have larger effective core sizes.

Figure 1B:
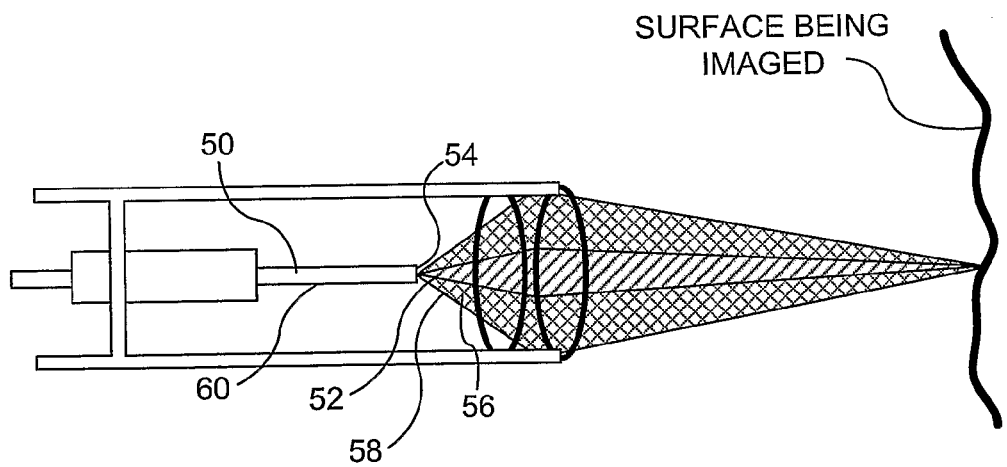
FIG. 1B illustrates an exemplary fiber scanning device that emits light from a singlemode core and collects light conveyed through an inner cladding of an optical fiber with dual cladding.

The collection of backscattered light can be augmented by using an optical fiber that has a singlemode core, and two concentric cladding layers, the inner cladding being used for the collection of backscattered light, as illustrated in FIG. 1B. The distal tip of a stationary dual-clad optical fiber 50 is shown to have two numerical apertures for the acceptance of light into the different waveguiding regions of the optical fiber. Typically the inner region (core) has a low numerical aperture and often a small core diameter 52. The numerical aperture of the core is shown as a cone, with its vertex at a core end face 54. Whereas, the inner cladding region of the dual-clad optical fiber typically has a much larger diameter 56, and has a higher numerical aperture, as shown by a larger cone angle 58, the outer cladding layer is often a thin polymer coating 60 of a lowest refractive index. The use of a more complex illuminating optical fiber, such as dual-clad optical fiber 50, provides the advantage of eliminating the surrounding collection optical fibers for imaging applications 26, enabling the entire endoscope tip diameter to be smaller.

For example, a cut-away view in FIG. 2A illustrates a variable radius or spiral scan mode of an optical fiber device 200. The scan mode shown in this Figure can be generated by driving an optical fiber 208 into a resonant (or near resonant) condition using a two axis piezoceramic tube actuator 206. In this exemplary embodiment, a plurality of light detectors 204 are arrayed around single piezoceramic tube actuator 206 in a simple arrangement, to produce signals indicative of the light received from a ROI, which is not shown in this Figure. Alternatively, a similar array of concentrically arranged and spaced-apart optical fibers 202 can convey light received at the distal end of the optical fibers from the ROI to light detectors (not shown) that are disposed at a proximal end of the optical fibers (e.g., outside the body of a patient). Piezoceramic tube actuator 206 concentrically surrounds optical fiber 208, and the optical fiber is tapered to a distal end 210. This tube actuator produces a driving force corresponding to a harmonic of a natural resonant frequency of optical fiber 208 so that the distal end of the optical fiber moves in an orbit 212 having an actuation controlled radius. The distal end of the scanning optical fiber corresponds to an optical point source that can be focused onto an illumination plane (not shown) by adding an imaging lens system 214. A major advantage of this embodiment is that it employs a single actuator and a waveguide that provide high resolution, directed illumination, and imaging within a relatively small diameter enclosure.

A series of variable radii circles are produced in a circular scan mode. The optical fiber can be driven in either mode during successive scanning frames. When driven in a spiral scan mode, the optical fiber produces a spiral scan in which the radius alternately increases and decreases. In an alternative scan pattern, the radius is increased in the desired pattern, and then the fiber is more rapidly returned to its centered position to begin the next frame. In either the circular or spiral scan modes, the distal end of optical fiber 208 scans an ROI to image the region and also renders therapy and/or diagnostic functions over the ROI. The whirling motion of the cantilevered optical fiber is controllably driven larger or smaller in diameter by increasing or decreasing the voltage applied to the four individual quadrants of piezoceramic tube actuator 206. Changes in the diameter of the scan can thus be made from one scanning frame to the next.

A "propeller" scan mode 216 is illustrated in FIG. 2B. In this scanning mode, the scanning optical fiber moves back and forth along different diameters of a circle, scanning the ROI. The rotation of the linear scan can be generated from the two-axis piezoceramic tube actuator or by simply rotating a single-axis actuator so that the axis of movement rotates in a corresponding manner about the longitudinal axis of the optical fiber. Again, the propeller scan mode can be used in successive scanning frames, or can be used in combination with either the linear, elliptical, circular, or spiral scan modes in successive scanning frames.

Instead of using a stationary imaging lens system at the tip of the endoscope, an alternative beam scanning embodiment 220 of the optical fiber device is illustrated in FIG. 2C. This embodiment uses a combination of a microlens 228 at the distal fiber tip, and a scan lens system 238. The use of microlens 228 on the distal end of optical fiber 226 produces a PSF that is consistently small across a wide field of view (FOV). The addition of a microlens to the resonant cantilevered waveguide structure creates a more complicated dynamic system than the previous point-source imaging embodiments shown in FIGS. 1A and 2A Beam scanning embodiment 220 includes a cylindrical supporting housing 222 in which is disposed a cylindrical actuator 224 of the piezoelectric or piezoceramic type that drives an optical fiber 226 to vibrate in a resonant 2-D scanning mode. Microlens 228 is fabricated at the distal end of optical fiber 226 for the purpose of generally collimating a scanned beam of light. The scanned beam 230 of light is focused by scan lens system 238 and describes an angle that is preferably greater than or equal to at least 40° relative to the longitudinal axis of the optical fiber and of cylindrical housing 222. When scanning, the center of the cantilevered portion of the optical fiber moves back and forth about this axis, as illustrated, while the point source of light emanating from the distal tip of optical fiber 226 remains generally stationary due to its inertial mass and the fact that the vibratory node is near the tip at a second node of resonance. The length of optical fiber 226 extending distally beyond actuator 224 and the mass of microlens 228 are selected to ensure that the scanning occurs with this form of motion. Light detectors 232 are disposed as an outer annulus of a scan lens 233 and in a base 235 around cylindrical actuator 224, which may be coated with a highly optical reflective material 237 (e.g., aluminum) to help channel the backscattered light to the detectors at high efficiencies. The light detectors may be optical sensors or may comprise the distal tips of collection optical fibers (with the option of including a microlens on each collection optical fiber for increased collection efficiency).

Theoretically, only a single light detector is required to collect the backscattered scanned light, to generate a monochrome or black and white image. A simple method for generating a full-color image is to use three light detectors, each covered with a different filter selected for blue, green, or red light transmission. Silicon-based semiconductor photodiodes (such as Si-PIN type) are preferred for visible and near IR light detection because of their high sensitivity, low cost, small size, high speed, and ruggedness. Photodiodes used routinely in the telecommunications industry, such as InGaAs material photodiodes, are preferred for embodiments of the present invention that use IR optical detection. Since the resolution of the integrated optical scanning technique does not depend on size and number of light detectors, all available space at the distal end of the optical fiber assembly can be covered with light detectors for the purpose of increasing and discriminating between signal levels. In at least one embodiment, the light detectors are provided in stereo-pairs about the optic axis so that topographical features (e.g., shadows) of the ROI can be enhanced and glare from spectral reflections can be diminished. If IR radiation is used in connection with visible light, then light detectors of different light-sensitive materials can be used without filters (not shown). An alternative method for separating the spectral response of a light detector that is not filtered requires synchronizing the detector signal in time with an appropriate illumination source having a pulsed output. For example, the same visible light detector can be used without any filters if the RGB laser or other light sources are individually pulsed in rapid time series and in synchronicity with the processing of signals received from the light detectors.

Leads 234 extend from each of the light detectors to the proximal end of the optical fiber, which is external to the patient's body, to convey the electrical signals from the light detectors to the external instrumentation, as discussed above. Actuator 224 is driven with an electrical signal supplied through leads 236, and the characteristics and timing of the electrical signal determine the scan pattern, amplitude, and other parameters of the scanning pattern executed in each successive scanning frame.

Exemplary Scanning System

FIG. 3 illustrates a system 350 that shows how the signals produced by various components that are inside a patient's body are processed with external instrumentation and how signals used for controlling the system to vary the scanning parameter(s) in successive scanning frames are input to the components that are positioned inside the patient's body, (e.g., on an endoscope). In order to provide integrated imaging and other functionality, system 350 is thus divided into the components that remain external to the patient's body, and those which are used internally (i.e., the components within a dash line 352). A block 354 lists the functional components disposed at the distal end of the scanning optical fiber system. As indicated therein, these exemplary components can include illumination optics, one or more electromechanical scan actuator(s), one or more scanner control actuator(s), one or more scanner motion detector(s) for control of the scanner motion, photon detectors for imaging the ROI, and optionally, additional photon detectors for diagnostic purposes and for therapy and monitoring purposes—one or more of which can be implemented using the same scanning device by varying the parameters of the scanning that are employed during different scanning frames. It should be noted that in regard to system 350, only the functional components actually required for a specific application may be included. Also, the additional functions besides imaging can be diagnostic, or therapy, or a combination of these functions.

Externally, the illumination optics and scanner(s) are supplied light from imaging sources and modulators as shown in a block 356. Further details concerning several preferred embodiments of external light source systems for producing RGB, UV, IR, and/or high intensity light conveyed to the distal end of an optical fiber system are either disclosed below or will be evident to a person of ordinary skill in this art. Scanner sensors can be used for controlling the scanning and produce a signal that is fed back to the scanner actuators, illumination source, and modulators to implement the scanning control after signal processing in a block 360. The sensors may simply be one or more temperature sensors, since temperature affects resonance and an open feedback system, based on initialization. Also, a temperature rise may occur due to the higher power therapy illumination transmitted through the system or indirectly as the result of thermal heat radiated back from the tissue.

In block 360, image signal filtering, buffering, scan conversion, amplification, and other processing functions are implemented using the electronic signals produced by the imaging photon detectors and for the other photon detectors employed for diagnosis/therapy, and monitoring purposes. Blocks 356 and 360 are interconnected bi-directionally to convey signals that facilitate the functions performed by each respective block. Similarly, each of these blocks is bi-directionally coupled in communication with a block 362 in which analog-to-digital (A/D) and digital-to-analog (D/A) converters are provided for processing signals that are supplied to a computer workstation user interface or other computing device employed for image acquisition, processing, for executing related programs, and for other functions. Control signals from the computer workstation are fed back to block 362 and converted into analog signals, where appropriate, for controlling or actuating each of the functions provided in blocks 356, 358, and 360. The A/D converters and D/A converters within block 362 are also coupled bi-directionally to a block 364 in which data storage is provided, and to a block 366. Block 366 represents a user interface for maneuvering, positioning, and stabilizing the end of the scanning optical fiber within a patient's body.

In block 364, the data storage is used for storing the image data produced by the detectors within a patient's body, and for storing other data related to the imaging and functions implemented by the scanning optical fiber. Block 364 is also coupled bi-directionally to the computer workstation 368 and to interactive display monitor(s) in a block 370. Block 370 receives an input from block 360, enabling images of the ROI to be displayed interactively. In addition, one or more passive video display monitors may be included within the system, as indicated in a block 372. Other types of display devices, for example, a head-mounted display (HMD) system, can also be provided, enabling medical personnel to view an ROI as a pseudo-stereo image.

Exemplary Scanning System for Imaging, Diagnosis, and Therapy

FIG. 4 illustrates the different functions that can be carried out with the scanning device in a scanning system 460, depending upon the instrumentation that is used. In this example, a single scanning waveguide is used for imaging, sampling diagnoses, and administering therapy, each function being done during different frames, by appropriately changing one or more parameters of the scanning process to enable the desired function to be achieved. It is helpful to recognize that by making small modifications to the components that are used as part of this scanning system, different functionality can be provided. For example, instead of providing diagnostic capabilities, the scanning system can be readily modified by changing a scanning parameter and other operational aspects of the scanning system, to monitor the progress of the therapy applied with the scanning system. In scanning system 460, an interactive computer workstation 462 enables medical practitioners to control the scanning optical fiber and to execute software algorithms used for imaging, diagnosis (e.g., by obtaining an optical biopsy), and administering therapy—all by the same scanning optical fiber during different scanning frames that are implemented with different scanning parameters. A high resolution color monitor 464 receives signals from a scanning optical fiber 484 that are conveyed over an optical fiber system 488 to a distribution console 472. Optional RGB detectors may be provided if not included internally within the patient's body adjacent to scanning optical fiber 484. A region of interest (ROI) 486 is scanned by the optical fiber to produce the high resolution color images displayed to a user.

In an exemplary passive display embodiment, two cathode ray tube monitors (CRTs) display images using two different contrast modes to generate the images of the same object (e.g., images of tissue at the ROI). For example, the same resonant driven scanning optical fiber may produce both a full-color optical image on one CRT and a grayscale fluorescence image on the other CRT monitor. If the optical properties of the excitation and signal do not overlap, then two or more images may be generated simultaneously. Otherwise, the two images are either captured in sequential frames or in alternating line sweeps of the fast resonant scanner. To switch between image contrast modes (full-color optical and fluorescence), the light sources are shuttered or directly turned off/on, depending upon the frame being implement with the scanning device. Synchronized in time during the modulation of both illumination power and spectral range, the signals from the photon detectors are recorded and displayed as separate images. In this example, by being provided with a second fluorescence image of the same ROI, a medical practitioner can find and positively identify small or pre-cancerous lesions that may or may not be visible on a standard white-light image produced during an imaging mode.

It is contemplated that one of the two displays might be a touch screen, or pad-, voice-, or joystick-controlled monitor that enables the medical practitioner to select (draw the outline) of an ROI for laser surgery. Since the image may be moving, the touch screen monitor will require the image to be captured and frozen in time. However, once this ROI is outlined, image segmentation and object recognition algorithms may be implemented to keep the ROI highlighted during real-time image acquisition and display. The touch screen monitor can provide sidebar menus for the practitioner to set parameters for the laser therapies, such as power level and duration of laser radiation exposure. The second display would not provide interactivity, but is preferably a high resolution monitor displaying the real-time optical image in full-color or grayscale. If IR photon detectors are integrated into the endoscope, the high resolution display with pseudo-color will allow the practitioner to monitor the progress of laser therapies, such as tissue heating and/or tissue irradiation in laser surgery.

The scanning optical fiber is positioned at a desired location within the patient's body, opposite ROI 486, using guide wires or a cannula (not shown) and a manual controller that facilitates tip navigation and stabilization, as indicated in a block 466. Within ROI 486, optical biopsy "spots" 485 illustrate the spatial and temporal distribution of single-point spectral measurements to diagnose for disease. These spots are distributed much like the current practice of invasively taking tissue samples for in vitro biopsy analysis. Each spot may be analyzed spectroscopically during a frame cycle of the optical scanner, separating $t_1$ and $t_2$ by, for example, about 1/30 second. In addition to the image provided by the scanning optical fiber, IR thermal photodetectors (and an optional temperature monitor) as indicated in a block 468 could be included for receiving IR signals from the ROI.

To facilitate control of the motion of the scanning optical fiber or light waveguide, electrical power for microsensors and control electronics are provided, as indicated in a block 470. The signals provided by the control electronics enable amplitude and displacement control of the optical fiber when the actuator that causes it to scan is controlled by both electrical hardware and software within block 470. A spectrophotometer and/or spectrum analyzer 474 is included for diagnostic purposes, since the spectral composition of light received from ROI 486 and distribution of optical biopsy locations 485 can be used for screening and diagnosis for such diseases as cancer to a medical practitioner in evaluation of the condition of the ROI, based upon spectral photometric analysis. To illuminate the ROI so that it can be imaged, red, green, and blue light sources 476, 478, and 480 are combined and the light that they produce is conveyed through the optical fiber system to scanning optical fiber 484. The light source used for spectral analysis may be a high power pulse from one of the RGB light sources (e.g., lasers), or a secondary laser or white light source. Since signal strength, time, and illumination intensity are limiting, a repeated single-point spectroscopic method can be initially employed, using flash illumination. In addition, the same or a different high power laser source 482 can be employed to administer therapy, such as PDT, the laser ablation of tumors, and other types of therapy rendered with a high intensity source. The scanning parameters associated with such therapy will clearly need to be different than those used for imaging and diagnosis. For example, the scan amplitude and scan frequency will likely be much less than used for imaging, to ensure that the therapeutic high intensity laser light is limited to the tissue needing it.

In using system 460, a medical practitioner navigates and maneuvers the flexible single scanning optical fiber component to an appropriate region of a patient's body while watching the high resolution color monitor displaying the standard, full-color endoscopic image. The search for tumors and/or pre-cancerous lesions begins by watching the monitor. A second monitor (not separately shown) included with spectrophotometer and spectrum analyzer 474 displays a fluorescence mapping in pseudo-color over a grayscale version of the endoscopic image. When an ROI is found, such as abnormal appearing tissue, the flexible endoscope is mechanically stabilized. The ROI is centered within the FOV, then magnified using the multi-resolution capability provided by the present invention. The size of the ROI or tumor is estimated, and a pixel boundary is determined by image processing either the visible image or the diagnostic image and possibly, by implementing a range finding to the ROI from the distal end of the scanner. If spectroscopic diagnosis is required, such as LIFS, the distribution of optical biopsy points is estimated along with illumination levels. The diagnostic measurements are performed by delivering the illumination repeatedly over many imaging frames automatically. The user can cease the diagnosis or have the workstation continue to improve signal-to-noise ratio and/or density of sampling until a clear diagnosis can be made. The results of diagnosis is expected to be in real-time and overlaid on top of the standard image.

Since the pixel dwell time for a resonantly scanned image is fixed for a certain FOV and image resolution, a single-point or single-pixel optical biopsy procedure may not have sufficient optical power or image stability to perform frame-sequential signal averaging. In these cases, a single optical biopsy "spot" will be selected, close to the center of the imaging FOV. Because the amplitude-modulated resonant scanning for normal imaging can be interrupted between frames, the diagnostic frame can be a single beam of illumination that is "parked" for an arbitrary period of time. The duration of the single optical biopsy "spot" can be determined by the user or by the system, having determined that sufficient signal has been acquired for an accurate diagnosis. The ability for not scanning during the diagnosis is the extreme case where the dwell time of light-tissue interaction is completely variable. In practice, the single optical biopsy spot may be enlarged slightly by non-resonant scanning of the illumination light or by resonant scanning in response to drive signals applied to the actuators that are significantly smaller in magnitude than those employed during the imaging frames. Exemplary drive signals are illustrated in FIGS. 5A-5H, along with some resulting scan patterns.

The diagnostic function that is implemented with the scanning optical fiber system (or other type of scanning device) can detect a fluorescence of tissue at a position in the region being scanned, which may be evidence of a physiological condition. Or the diagnostic function might determine either a fluorescent or phosphorescent lifetime at a desired position in the region. Other diagnostic procedures that can be performed include conducting a laser-induced fluorescence spectroscopic analysis at the desired position in the region being scanned, conducting a white light reflectance spectroscopic analysis at the desired position, and conducting a Raman spectroscopic analysis at the position. Additional diagnostic and therapeutic procedures that can be performed include a multi-photon investigation of the ROI using multi-photon excitation of fluorescence, second harmonic generation of photons, and the destructive power of multi-photon ablation for optical therapy in situ. Diagnosis may include accurate mapping of distances and depths, for example, by implementing range finding between the endoscope and tissue for estimating size or coherence imaging, or optical coherence tomography line scans for estimating depth of structures within tissue, such as tumor penetration. Those of ordinary skill will readily understand how appropriate light sources and scanning parameters can be applied to achieve each of these diagnostic functions.

If optical therapy is warranted, such as PDT, then an optical radiation exposure is determined and programmed into the interactive computer workstation controlling the scanning optical system. The PDT treatment is an optical scan of high intensity laser illumination typically by high power laser source 482, pre-selected for the PDT fluorescent dye, and can be controlled using dichroic filters, attenuators, and electro-mechanical shutters. In a frame-sequential manner, both fluorescence images and visible images are acquired during PDT treatment using the same scanning device, by controlling the scanning parameters to achieve the appropriate scanning for each functionality in different scanning frames. The medical practitioner monitors the progress of the PDT treatment by observing these acquired images on both displays.

Similar to the integration of resonant optical scanning and optical diagnosis, the dwell times for individual pixels within the image frame may be insufficient to cause the desired therapeutic effects, such as laser ablation or thermal necrosis, when optical illumination intensity is simply increased. Therefore, the resonant scanning used for imaging may need to be turned off or interrupted, and the illumination "parked" over a certain ROI for therapy. The ability to park the illumination at the central pixel in the imaging field on a frame-sequential basis enables the dwell time of light-tissue interaction to be arbitrary or selectively defined by the user and not dependent upon limitation of the imaging system. Long dwell times may be required for laser hole drilling or single point laser ablations. Although single point optical biopsy "spots" may be sufficient to determine a diagnosis, the entire ROI must be treated for an optical therapy in most cases. Therefore, the holes being drilled may be predetermined to fill an entire area, such as when a large hole is bored by making many smaller holes in a pattern. Between each hole drilled or after many holes have been drilled, the ROI can be re-imaged in a frame-sequential manner. Each hole can be enlarged slightly by scanning at a non-resonant frequently or by scanning at very low amplitudes at or near the resonant frequency used for imaging. By scanning a much smaller area than that covered by the imaging frame, the dwell times at each pixel position is increased by the slower translation of the scanned spot. Exemplary drive signals are illustrated in FIGS. 6A-6D and 7A-7F, along with resulting scan patterns.

Various types of optical therapy can be delivered using the scanning device, by providing an appropriate intensity light source and controlling the scanning parameters of the scanning device drive signal to achieve a desired pattern and other appropriate characteristics. In a frame-sequential manner the control of this therapy can be monitored either by imaging between repeated does of therapy, or by providing a separate monitoring function, such as infrared thermal imaging or blood flow imaging frames. For example, if the region being scanned is the eye of a patient, the scanning device can be used to deliver a laser illumination photoactivation by releasing a molecule, or a laser optoporation procedure, or a vision modification procedure, and then by switching parameters and the light source used, medical personnel can determine the efficacy of the therapy, assess any signs of damage, and/or determine if further therapy is needed.

Examples of Successive Scanning Frames and Resulting Scan Patterns

FIGS. 5A-5H illustrate several examples of the different scanning parameters that be employed in successive scanning frames. All of FIGS. 5A-5H illustrate the exemplary case of a spiral scan of a resonant fiber scanner with the drive signals to the two-dimensional actuator for lateral vibration of the cantilevered optical fiber set to equal frequency and amplitude. However, only one axis of drive signal is shown in FIGS. 5A-5H, which is labeled the X-drive axis. Typically, the Y-drive axis is nearly identical in amplitude and frequency, but is phase-shifted to create a desired pattern, for example, by 90-degrees to generate a circular resonant motion.

Figure 5A:
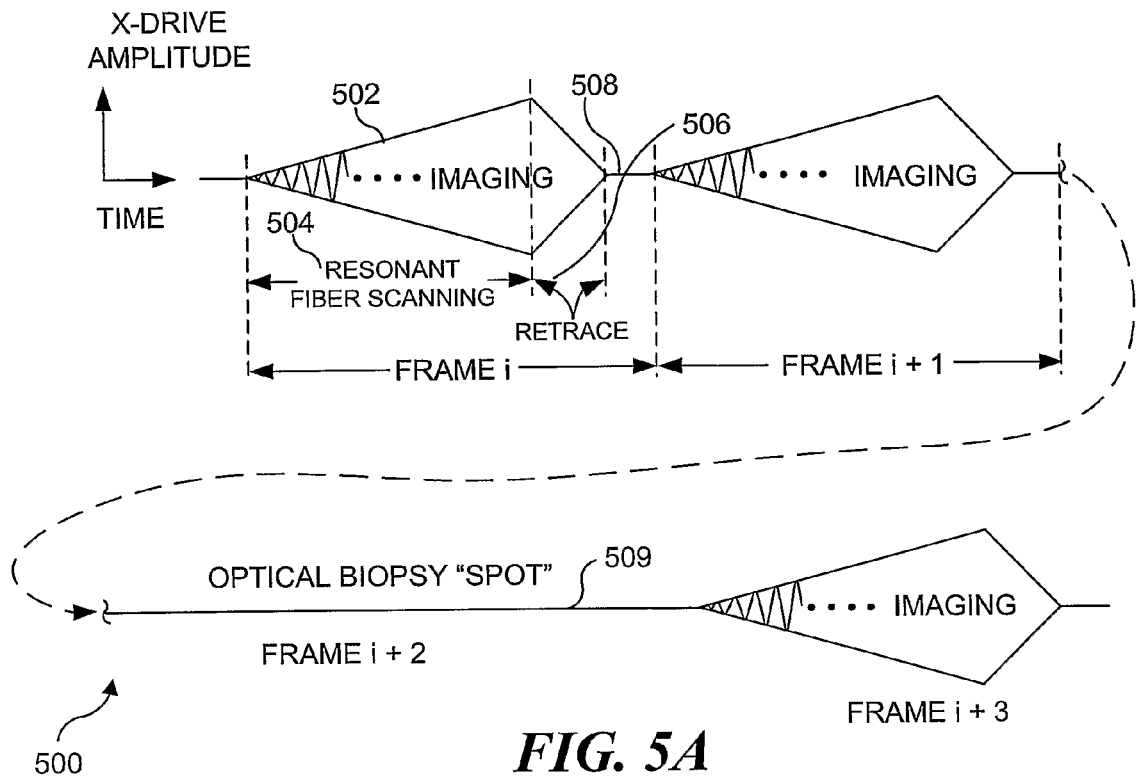

In FIG. 5A, a plurality of scanning frames 500 are illustrated in which each successive scanning frame 502 is identical, but the scanning device is stopped for an arbitrary or selected interval of time, depending on the function required of the resonant scanning device. In this case, the repeated scanning frames represent the continuous imaging mode of normal operation of a scanning fiber endoscope. Within each imaging frame, there is a time that the resonant fiber scan is driven into an expanding spiral pattern, as identified by an expanding spiral duration 504. After full expansion of the spiral scan, there is a period of time for repositioning the fiber back to the starting position before another imaging frame, i.e., a retrace time 506, and a minimum settling time 508, which is used for settling the resonant amplitude to zero. All time intervals are selectively adjustable by the user (or automatically by the system) depending on the functions required of the scanning frames. In this example, the repeated imaging frame that is defined by expanding spiral duration (ESD) 504, time to retrace 506, and minimum settling time 508 is identical with the first imaging frame illustrated as frame i. A subsequent imaging frame is indicated by i+1. After this second imaging frame, settling time 508 can be expanded in time arbitrarily for a diagnostic function during a frame i+2, as shown in FIG. 5A as a reference number 509. This diagnostic function can maintain the fiber scanner in a stationary position for an arbitrary length of time to allow sufficient optical power to perform an optical biopsy diagnosis at a single location or "spot," as defined earlier. The interrupted resonant fiber scanning for imaging is resumed in a subsequent frame i+3.

Figure 5B:
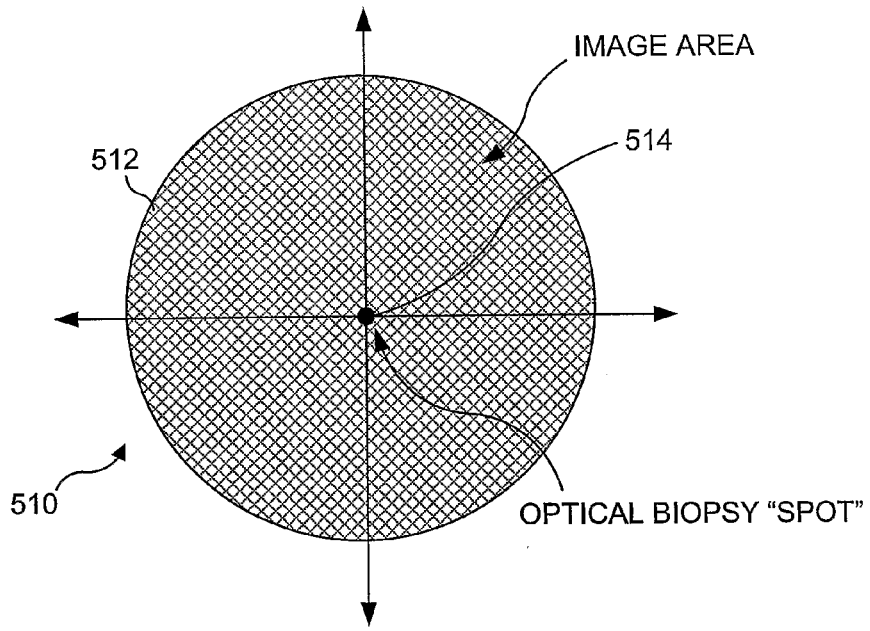

The expanding spiral scan used for imaging is symmetrical about the origin of the X and Y drive axes, resulting in a circular two-dimensional scan pattern 510 shown in FIG. 5B. The three imaging frames i, i+1, and i+3 from FIG. 5A, each scan a circular area 512 in FIG. 5B. The single optical biopsy "spot" is located at an origin or center 514 of circular area 512. All representations of the 2-D scan pattern from successive imaging frames that are interrupted by frames employed for other carrying out functions assume that there is no motion other than the fiber scanning motion, i.e., that the endoscope remains stationary.

In FIG. 5C, a plurality of scanning frames 520 is illustrated in which scanning frame 502 is followed by settling time 508 in which the scanning device is stopped, and the scanning device is next driven, as shown in a scanning frame 522. In scanning frame 522, the scanning device is driven up to twice the maximum amplitude of frame 502, but at a substantially lower frequency than in scanning frame 502, and the duration of scanning frame 522 is longer than that of scanning frame 502. In this example, the frequency within the imaging frame is at or near the resonance of the fiber scanner, while the frequency within the subsequent diagnostic frame is substantially less than the scanner resonance. Due to the lack of mechanical amplification of the scanner response at a non-resonant frequency, the larger amplitude of the X-drive signal will serve to expand the single diagnostic spot only slightly, as shown in FIG. 5D. A round imaged area 532 in a 2-D scan pattern 530 in FIG. 5D is exactly the same as circular area 512 in FIG. 5B; however, a single biopsy spot 534 in FIG. 5D is slightly enlarged by the non-resonant scanning, compared to circular area 512 from FIG. 5B.

Figures 5E, 5F:
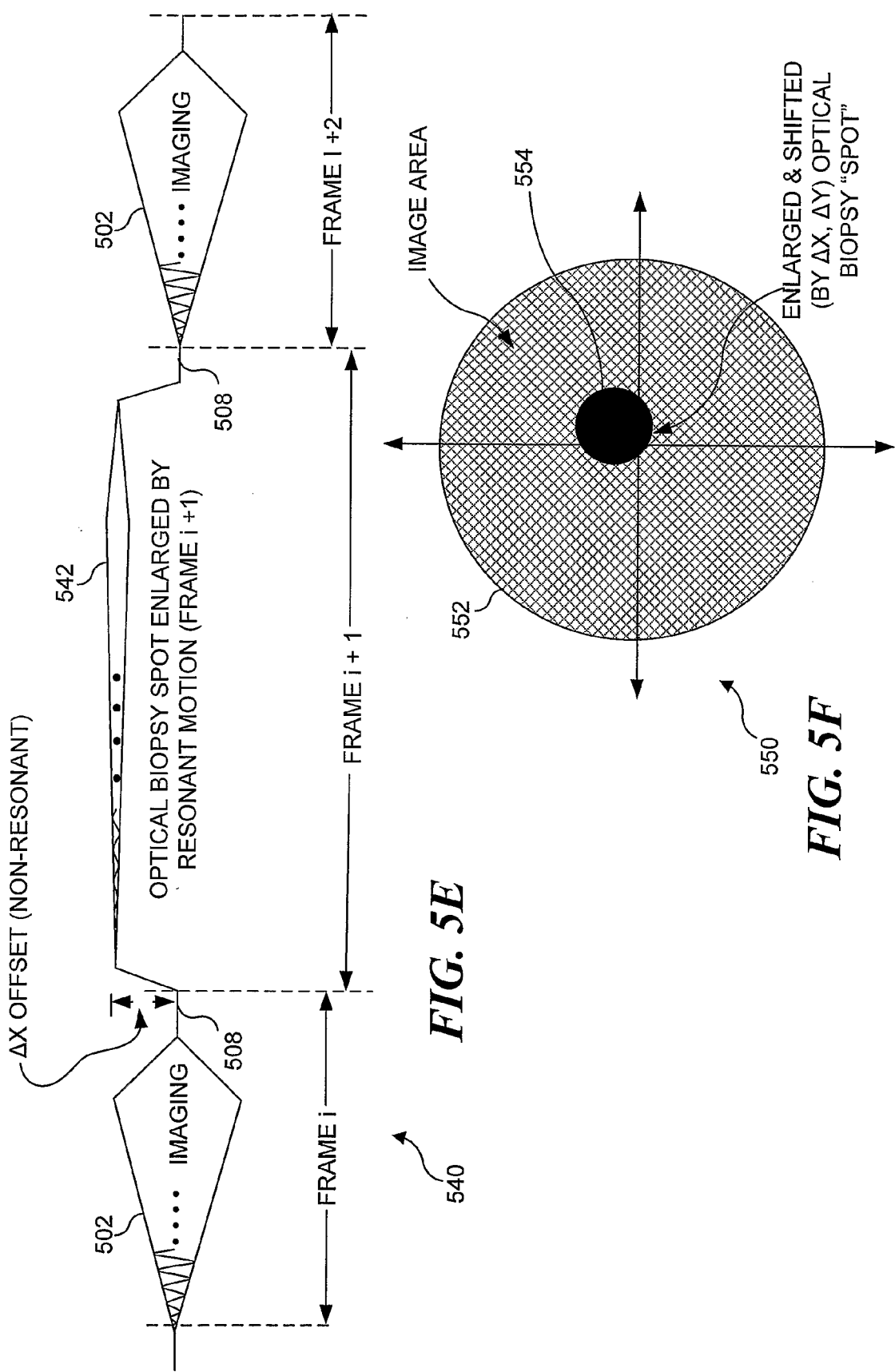

In FIG. 5E, a plurality of scanning frames 540 is illustrated in which scanning frame 502 is followed by settling time 508 during which the scanning device is stopped before starting to drive the scanning device in a scanning frame 542. In scanning frame 542, the scanning device is driven by the combination of both a periodic signal (AC-signal) at very small amplitude and having a steady-state offset (DC-offset) at large amplitude. In contrast to the example shown in FIG. 5C, where the biopsy spot in the diagnostic frame is slightly enlarged by a large-amplitude non-resonant scan, the small-amplitude periodic signal during the diagnostic frame in FIG. 5E is at or near the resonant frequency, allowing mechanical amplification of motion. As shown in a 2-D scan pattern 550 in FIG. 5F, a resulting optical biopsy spot 554 is enlarged and offset from the origin or the center of an imaged field 552 due to the applied DC-offset. The non-resonant DC-offset can also shift the single optical biopsy spot axially (or in depth), as well as laterally. The DC-offset can be applied to an actuator that shifts the point source closer to the lens system, which will increase the focal depth. For example all four quadrants (+X, −X, +Y, −Y) of the tube piezoceramic actuator can be activated equally to effectively enlarge the tube structure, by moving the fiber tip toward the lens system without displacing the point source laterally. Another actuator (not shown) can be activated with a DC-offset to optically zoom and change the depth of the scanned illumination plane and the location of the optical diagnosis.

In FIG. 5G, a plurality of scanning frames 560 illustrates a series of alternating imaging frames with the scanning device operated at interrupted resonance (illustrated with the X-drive signals only). In this example, a drive signal 562 for frame i generates a resonant fiber-scanned image that has twice the amplitude, but one-half the ESD as the resonant fiber-scanned image of frame i+1 that is produced with a drive signal 564. Since both frames are imaging at or near the fiber scanner resonance frequency, the expanding spiral duration determines the number of scan lines (circles) within the imaged field. The maximum amplitude of the drive signal determines the maximum amplitude of the fiber scanner, which directly relates to the imaged field of view. However, if both images are displayed at equal resolution concurrently on a display screen 570 of equal pixel mapping, then a resulting image 572 from frame i would be half the diameter of an image 574 from frame i+1 as shown in FIG. 5H. Typically, the image frame of larger field-of-view (frame i) would be displayed to the user across a larger display area than the image frame of smaller field-of-view (frame i+1), so in practice, two different displays will be used or the formatting of the images can be adjusted to accommodate the user's expectations. The use of continuously changing drive signals applied to a resonant optical scanner in a time series illustrates that the resulting two displayed images can be concurrently displayed to the user.

Figure 6A:
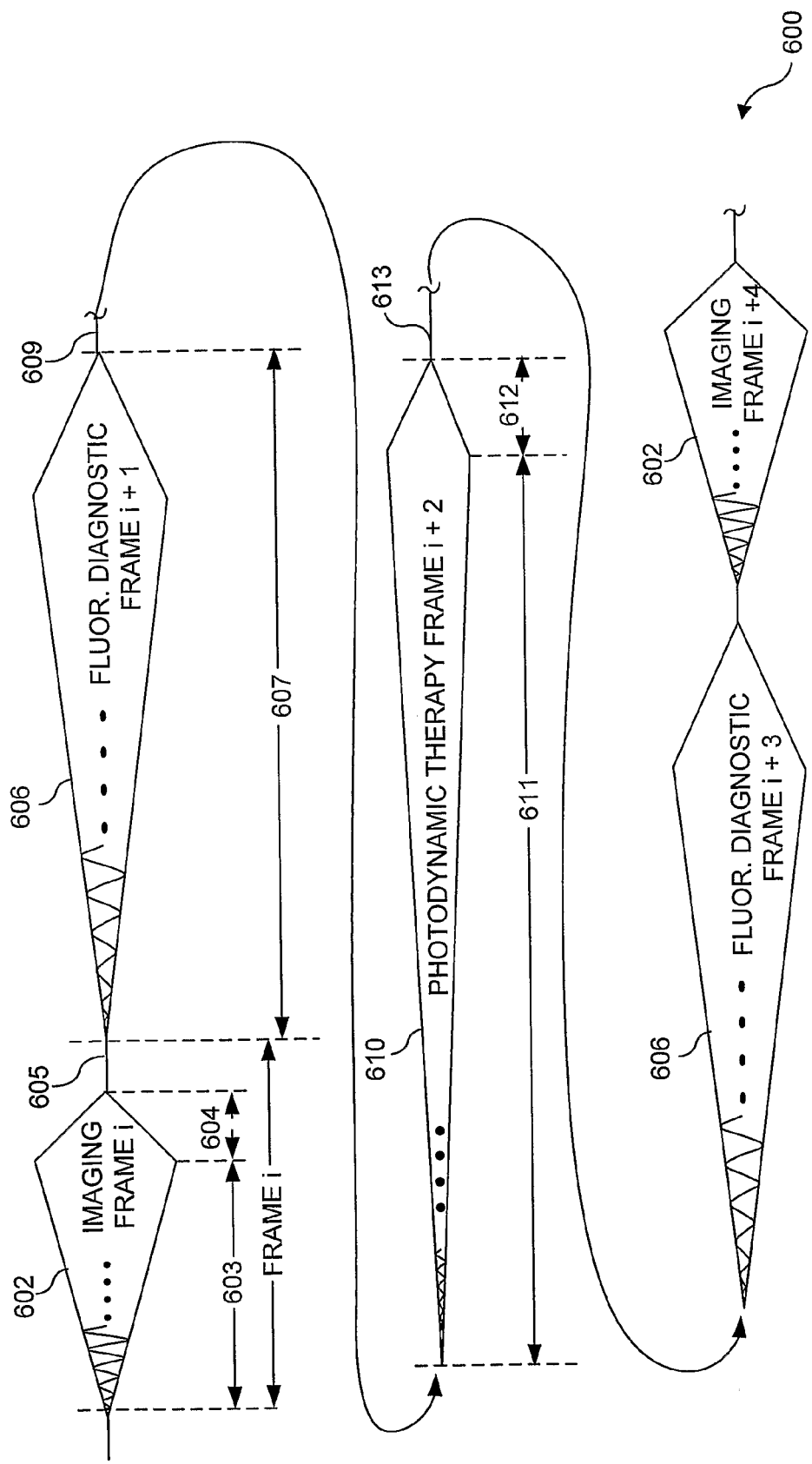

A plurality of imaging frames are interrupted by both diagnostic and therapeutic frames in an illustrative example 600 of FIG. 6A. As indicated therein, the X-drive signal over a series of five frames are shown for driving a resonant fiber scanner while the Y-drive signal is expected to appear similar, but 90-degrees out of phase (for spiral scanning). An initial frame 602 is the standard imaging frame i that was represented in FIG. 5A. An expanding spiral duration 603, a retrace time 604 and a settling time 605 separate the imaging frame i from a subsequent diagnostic frame 606, i.e., diagnostic frame i+1. The diagnostic frame (i+1) can be a fluorescence image that may require more light-tissue interaction dwell time per unit area than the imaging frame (i), which requires a ESD 607. The duration of retrace time 608 and a setting time 609 are expected to be the same as for the imaging frame, since the field of view is about the same (same maximum amplitude). A subsequent therapeutic frame (i+2) requires the longest light-tissue interaction dwell time per area, so an expanding spiral duration 611 is maximized, while a retrace time 612 and a settling time 613 can be equal to or shorter than previous frames having a larger FOV. The therapeutic frame (i+2) can be for photodynamic therapy, exciting the same fluorescent sensitizer that was imaged in the previous diagnostic frame (i+1), but at much higher power and over a smaller area. The following frame represents a repeated diagnostic frame (i+3) like diagnostic frame 606 that images the same fluorescence emission spectrum from the previous diagnostic frame (i+1). The repeated fluorescence diagnosis can give the user a measure of residual fluorescence activity, which may correlate to the prospect of repeating the photodynamic therapy. A final frame (i+4) (like initial frame 602 represents a series of repeated imaging frames. These exemplary sequential frames correspond to what is expected to a typical operation of an endoscope using the present approach.

Figure 6B:
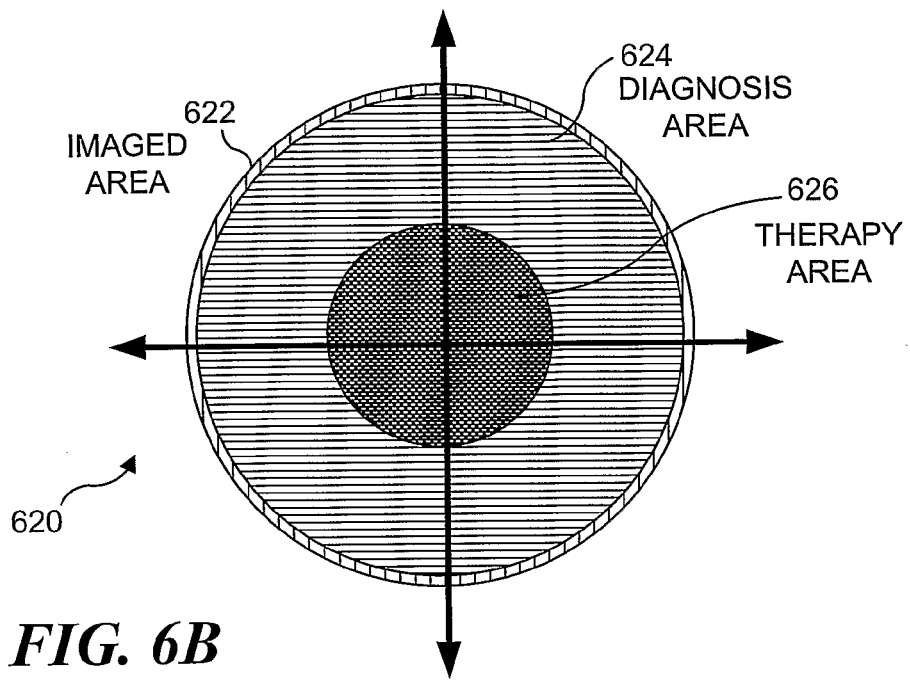

The 2-D scan patterns of the exemplary X-drive signals that result in imaging, diagnosis, and therapeutic frames in time sequential series can be superimposed, as illustrated in FIG. 6B. Superimposed spiral scan patterns 620 are shown as the imaged area with a vertical line fill 622, a fluorescence diagnosis area with a horizontal line fill 624, and a smaller therapeutic PDT area (as dark fill) (626). Since no offset voltages were used in the drive signals, all scanning patterns are centered at the origin. Also, since both X and Y drive signals were assumed to be matched in frequency and amplitude, the scanning patterns are circularly symmetric.

Figure 6D:
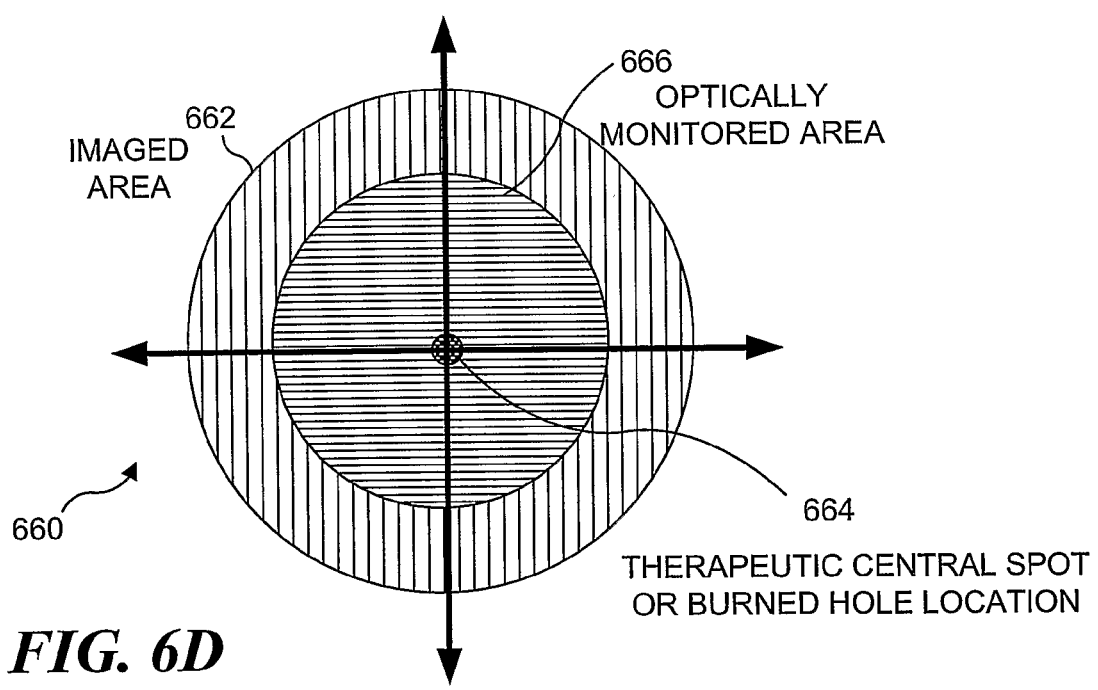
Figure 6C:
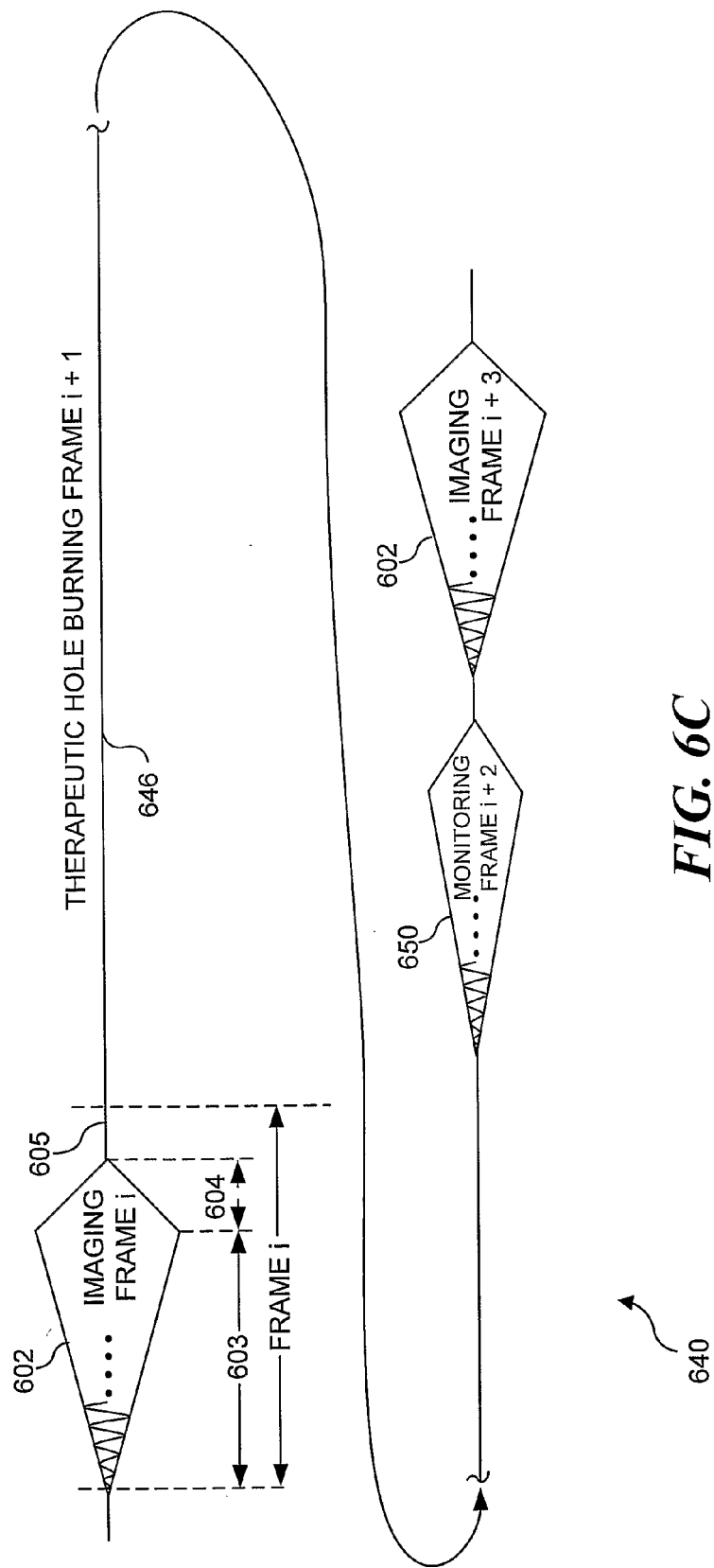

FIG. 6C illustrates an exemplary set of consecutive frames of imaging, therapy, monitoring, and imaging 640 produced with the X-drive signal required for generating the resonant fiber scans. A first imaging frame (i) 602 has an expanding spiral duration 603, retrace time 604 and settling time 605 as shown in FIG. 6A. A subsequent therapeutic frame (i+1) 646 provides a stationary or single point of therapy for an arbitrary amount of time. Long periods of light-tissue interaction are required for therapies such as thermal heating and thermal necrosis. Immediately following the therapeutic frame is a monitoring frame (i+2) 650, which is employed to assess the tissue response to the optical therapy applied and to assess whether therapy should be repeated. The monitoring frame can use infrared imaging to assess the depth of damage, or thermal mapping to assess the temperature of the tissue. The series of frames ends with a repeated imaging frame (i+3), which is identical to initial frame 602.

FIG. 6D illustrates resulting 2-D scan patterns 660 produced from the X-drive signals of FIG. 6C. All three scan patterns of imaging, therapy, and monitoring are superimposed. An imaged area 662 is the largest circular area, while a therapeutic central spot 664 is disposed at the origin, since there was no scanning. A scan 666 for monitoring was at one-half the maximum drive amplitude of scan 662 for imaging, so the area is shown at one-half the diameter of scan 662.

Figure 7A:
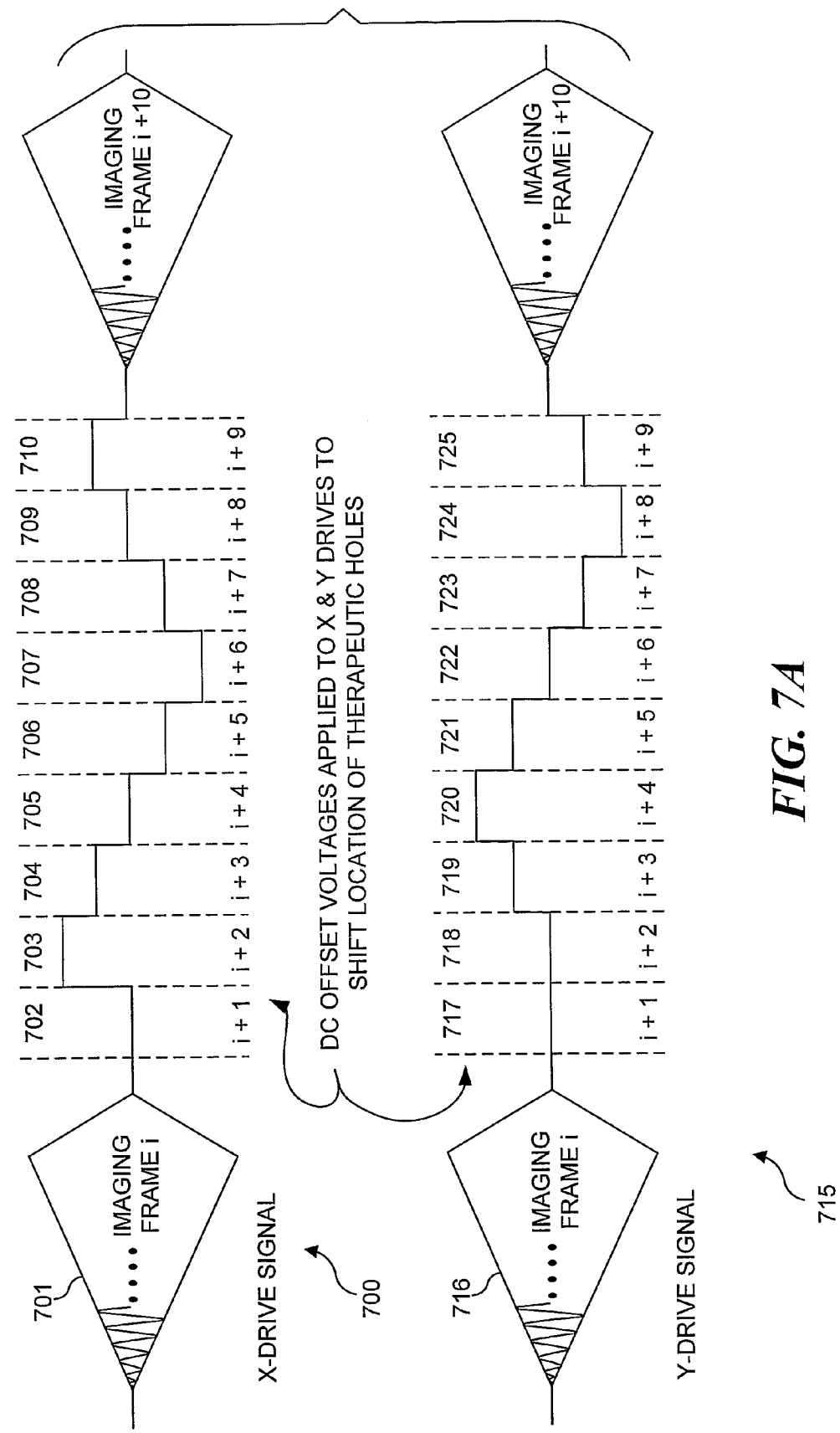

The scanning signal that drives a scanning device can be driven in two orthogonal directions, i.e., in an X direction and a Y direction, as shown by input signal waveforms 700 and 715, in FIG. 7A. Input signal waveform 700 includes an initial frame (i) and a final (i+10) scanned image frame 701, which are separated by nine separate therapeutic frames (i+1 through i+9) 702 through 710. At each of the separate scanning frames, the X-drive signal is shifted by a DC-offset voltage indicated by the amplitude of the stepped voltage signal. Similarly, Y-drive signal waveform 715 includes an initial frame (i) and a final (i+10) imaging frame 716 separated by nine therapeutic frames (i+1 through i+9) 717 through 725. A separate set of DC-offset voltages for the Y-drive signal produce a central point and eight surrounding points of fixed-point illumination. The X and Y input signal waveforms 700 and 715 represent the same total time interval. While the resonant scan frequency is the same in all the amplitude-modulated imaging scans, the Y-scan drive signal is shifted 90-degrees out of phase with the X-scan drive signal in input signal waveforms 700 and 715 to generate a spiral scan using a resonant fiber scanner.

Figure 7B:
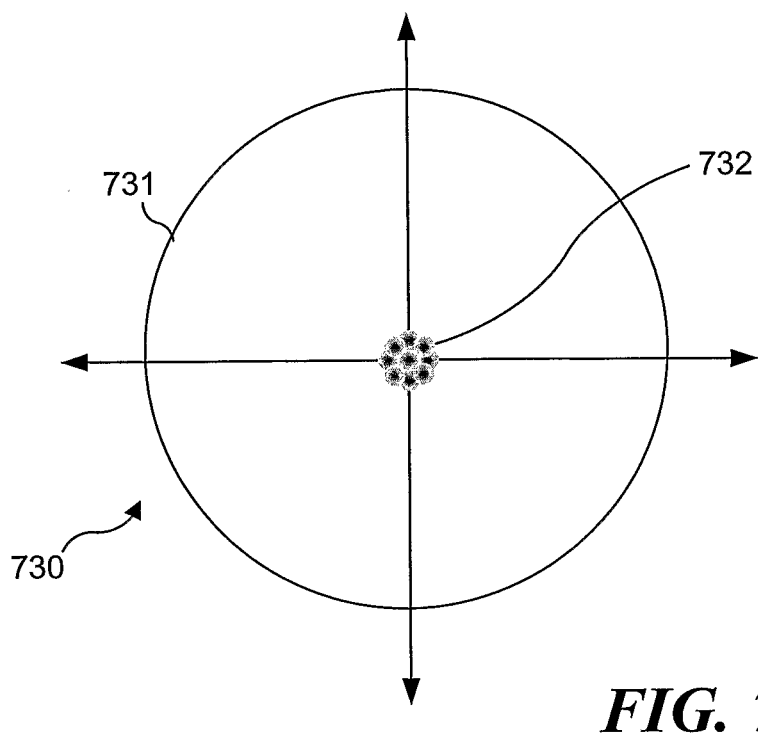

Exemplary scan patterns 730 from waveforms in FIG. 7A are shown in FIG. 7B. Nine therapeutic spots 732 are shown superimposed on a circular imaged area 731. In comparison to single therapeutic spot 664 in FIG. 6D, which was made over a long duration of thermal heating, nine smaller therapeutic spots 732 in FIG. 7B are produced over a shorter duration of laser ablation resulting in hole drilling. To cover a larger area about the central origin of imaged area, the therapeutic hole drilling is shifted laterally in a times series by applying eight different non-resonant DC-offsets to the X and Y drive signals shown in FIG. 7A. The applied DC-offset can also be in the axial Z-direction, which would expand the hole depth more than the ablation area.

In FIG. 7C, two orthogonal diagnostic line scans 750, and 760, respectively, are introduced within a series of scanned imaging frames that have different exemplary scanner inputs (drive signals) for the X and Y directions. The first (i) and last (i+3) frames are resonant scanned image frames 701 and 716 for X and Y drive signals respectively. For the X-drive signal, the next frame in time (i+1) is a resonant line scan along the horizontal or X axis that is repeated for an arbitrary time 752. A corresponding Y axis drive signal 762 during this repeated horizontal line scan is zero, since no amplitude is required in the direction orthogonal to the X-axis. The subsequent frame (i+2) is a resonant line scan along the orthogonal vertical Y axis that is repeated for an arbitrary time 754 for the X-drive, and arbitrary time 764 for the Y-drive. Since the line scan is only along the vertical or Y axis, there is no amplitude during this frame (i+2) for the X-drive, but there is full amplitude for the Y-drive signal. Each of the linear scanning patterns (horizontal and vertical) are repeated resonant line scans for an arbitrary time period that can be defined by the diagnosis procedure being carried out. Since the scan pattern remains the same during each diagnostic period, the resulting diagnostic line scans in orthogonal directions are referred to as two frames (i+1) and (i+2).

Figure 7D:
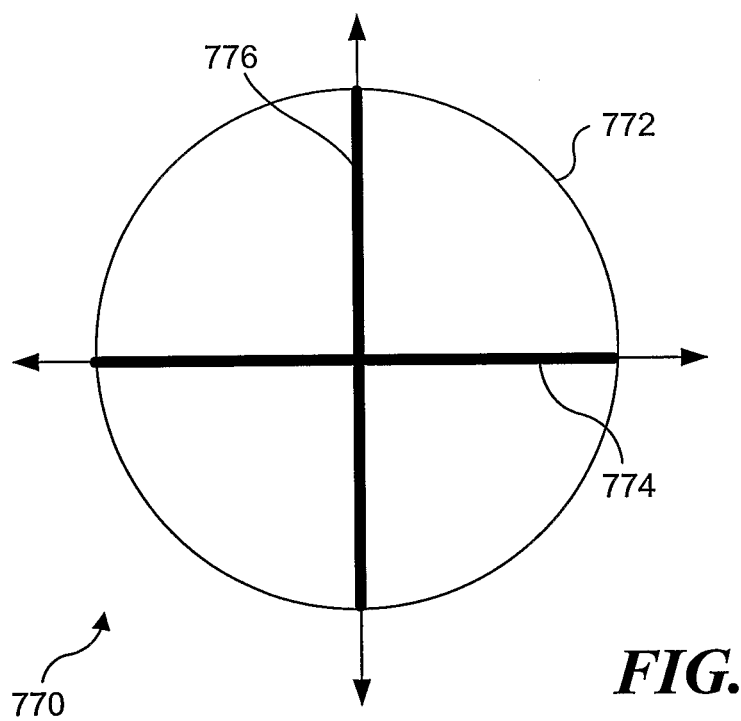

The 2-D scanning patterns of the imaging and diagnostic frames are illustrated in FIG. 7D. A round imaged area 772 is centered at the origin of the vertical and horizontal axes. The two orthogonal linear scans are repeated along a horizontal axis 774 and a vertical axis 776 within the imaged circular area, since the maximum amplitudes of the resonant drive signals for imaging and diagnosis are the same.

The repeated diagnostic line scan can have several functions. By scanning over the same area repeatedly, a weak diagnostic signal scan be averaged at each pixel to increase the signal-to-noise ratio. Alternately, the light source can be tuned or filtered to different spectral regions of scanned illumination to conduct multi-spectral or hyper-spectral analysis. Additionally, the focal depth may be changed over the repeated line scans to measure diagnostic optical fluorescence or backscattered light (optical coherent tomography signal) over increasing depth to create a cross-sectional view or slice through the tissue structures.

FIGS. 7E and 7F illustrate a plurality of resonant scanned imaging frames that are interrupted with one or more frames for diagnosis, therapy, and/or monitoring and which have a scan area that is selectively determined in size, in order to match the desire of the user or to match the geometry of the ROI. In FIG. 7E, the different inputs to the X-drive (solid line) and Y-drive (dashed line) signals 780 are illustrated as described below, using a resonant fiber scanner with spiral scanning pattern. First (i) and last (i+2) imaging frames 782 represent continuous imaging before and after either a diagnosis, therapy, and/or monitoring frame (i+1) 784. Frame (i+1) 784 has a maximum X-drive signal amplitude 786 that is twice a Y-drive signal amplitude 788. In comparison to the previous and subsequent imaging frames, the X-drive signal for the amplitude-modulated resonant scanning is over twice the duration but less than the maximum amplitude of the imaging frame. In FIG. 7F, the resulting 2-D scan patterns are illustrated as a superposition 790. A circular imaged area 792 is centered about the origin, while an elliptical area 794 that defines a diagnostic, therapeutic, or monitored region is smaller, with its greatest dimension along the X-axis. The elliptical area is centered about the origin, since no offset voltages were applied in this example.

The examples of interrupted resonance scanning for the purpose of varying the implementation of a function such as imaging, diagnosis, therapy, and monitoring in a frame sequential manner were all illustrated using a resonant fiber scanner and mostly in a spiral scanning mode of operation. Normal operation of the spiral scanning frame can eliminate the fast retrace and settling time for the resonant fiber scanner and operate with a continuous triangle wave for the amplitude modulation waveform that may never go to zero amplitude of resonant fiber motion (for example, see "Modeling and Control of the Resonant Fiber Scanner for Laser Scanning Display or Acquisition," Smithwick et al., page 1455, SID '03 Digest, (2003), which describes the use of triangle waves with and without feedback control). Other scanning patterns can be implemented with a scanning fiber with minor modifications, such as Lissajous scan patterns (for example, see "A Miniature Head-Mounted Two-Photon Microscope: High-Resolution Brain Imaging in Freely Moving Animals," Helmchen et al, Neuron, Vol. 31, 903-912, Sep. 27, 2001, Copyright 2001 by Cell Press). Finally, the optical scanner can be used for illumination only, illumination and detection, or detection of optical signals only.

Exemplary Moving Mirror Scanning Devices

FIG. 8 illustrates a first embodiment of an exemplary scanning device 800 for use in an endoscope that uses a moving micro-electro-mechanical system (MEMS) reflective surface 818 for scanning a region 840. A single mode optical fiber 810 conveys an optical signal 816, producing an expanding beam, for example, with a numerical aperture approximately equal to 0.11. A vertical drive actuator 812 and a horizontal drive actuator 814 bi-axially move the reflective surface in the X and Y directions relative to a centerline 838. An orifice 820 is formed in the MEMS reflective surface to enable the expanding light beam to pass through the MEMS reflective surface along a path 826 toward a fixed convex mirror 824. The light beam is reflected from the fixed convex mirror along a path 828, and then reflected from the MEMS reflective surface along paths 830 toward scan lenses 832 and 834, which focus the light beam onto a point 836 that scans over region 840. It should be noted that MEMS reflective surface is not required to be concave (as shown in the Figure), but can instead be flat so that it does not provide any optical power for focusing the light beam. Furthermore, the MEMS mirror surface can be manufactured to be varied dynamically (for example, see Yuhe Shao et al., "MEMS Three-dimensional scan mirror, In MOEMS Display and Imaging Systems II," edited by Hakan Urey et al., Proceedings of the SPIE Vol. 5348: 175-183, 2004). In this case, the optical system can still converge the light beam to a desired focus at point 836 that is distal of the distal end of the endoscope. A planar (rather than a concave) MEMS reflective surface would actually be easier to manufacture at a high optical quality. The bi-axial scanning of the MEMS reflective surface necessary to provide a sufficient FOV for an endoscope would likely require the MEMS reflective surface to move in a resonant or near resonant motion. However, a non-resonant movement of the MEMS reflective surface may be sufficient for a microscopic FOV, (e.g., less than 1 mm in diameter).

A second exemplary embodiment of a moving mirror scanning device 900 that can be used, for example, in an endoscope, is illustrated in FIGS. 9A and 9B. Scanning device 900 differs from scanning device 800, because it uses two separate reflective surfaces for the two orthogonal axes, one for the X axis and one for the Y axis. Each reflective surface is thus driven to scan only in regard to one axis. A resonant drive 902 will be used to drive a reflective surface 904 to move back and forth in the horizontal direction. Most likely, resonant drive 902 and scanning reflective surface 904 will comprise a resonant MEMS scanner. A single mode optical fiber 910 conveys a light beam 912 toward a flat reflective surface 906 that serves to vertically scan the beam and is mounted on a shaft 908a. Shaft 908a is driven to oscillate back and forth by a vertical drive 908 that, being smaller than the horizontal scanner, operates at a resonant or near resonant state with a fast fly back, (e.g., at the frame rate of the raster scan). The light beam is reflected from flat reflective surface 906 along a path 914 toward horizontally scanning reflective surface 904 and is reflected thereby along a path 916 and through scan lenses 918 and 920. These scan lenses focus the light beam to a point 922 on a region 940, so that the point scans over the region in a desired pattern determined by the signal that drives the vertical and horizontal scanners.

Scanning device 900 is illustrated as having a non-confocal geometry. Light from the region resulting from the scanning travels back through scan lenses 920 and 918, along an exemplary path 924, and into an optional collection optical fibers 926, 928, and 930, which may be provided with red, green, and blue filters, or with other waveband filtering. The optional collection optical fibers can be placed either outside the scanning device portion of the endoscope that includes the lenses, or may surround the MEMS reflective surface comprising the vertical scanner, as shown. In addition, a single mode RGB optical fiber 910, as well as other optional optical fibers 932, 934, and 936 can be provided to implement other functions. For example, optional optical fiber 936 can be a single mode optical fiber that conveys a high intensity light beam produced by a high power laser for rendering therapy to a desired portion of region 940, using the two scanners.

An embodiment of a small-core optical fiber that has been conditioned to increase the optical damage threshold is shown in FIG. 10. In this illustration, light 1010 that is to be conducted through an optical fiber 1050 is first passed through a coupling lens 1020 to focus the energy. An optional aperture 1030 may be used to control the diameter of the light beam as it converges onto the small core of optical fiber 1050. A precisely controlled diameter will ensure that there is minimal stray light that could be absorbed and lead to optical damage. On the front face or proximal end of the small-core optical fiber 1050 is mounted an end cap 1040. End cap 1040 is made of the same or a material similar to that of the core of the optical fiber and is essentially just a larger diameter component that reduces the intensity of light deliver to the proximal interface. Cap 1040 enables minimal absorption to take place at an interface 1060 and eliminates the possibility of adsorbed contaminates, where the optical intensity is the greatest, by providing a continuous medium for the light to propagate locally. Since end cap 1040 and optical fiber 1050 are made of the same or similar material, interface 1060 will exist only symbolically and not physically, providing that a high quality splicing or fusing process has been used for joining end cap 1040 and optical fiber 1050 into one continuous unencumbered medium. The interface between air and the medium will effectively be moved to an interface 1070 disposed at the proximal end of the end cap.

Interface 1070 can be conditioned using a mechanical or optical polish to reduce the amount of optical absorption at this interface. A mechanical polish involves grinding the surface of interface 1070 with a successively finer abrasives until the surface is free from scratches, pits, etc. An optical polish involves irradiating the surface of interface 1070 with a high power infrared light sourced so that a plasma forms for a short time on the surface. When the plasma cools and the material resets, any residual scratches, pits, etc. will have been removed. The surface of interface 1070 can also be coated to minimize reflections at the selected optical frequencies. Finally, light conductive optical fiber 1050, with end cap 1040, focusing lens 1020, and optional aperture 1030, can be hermetically sealed within an internal enclosure 1080 so that no contaminants are allowed to form on the surface of interface 1070. An X Y Z micropositioning system 1090 can be added to the optical fiber plus end-cap system to provide compensation for any thermal drift of position due to the transient introduction of high power optical energy used for therapy.

Although the present development has been described in connection with the preferred form of practicing it and modifications thereto, those of ordinary skill in the art will understand that many other modifications can be made to this technology within the scope of the claims that follow. Accordingly, it is not intended that the scope of the development in any way be limited by the above description, but instead be determined entirely by reference to the claims that follow.

The invention in which an exclusive right is claimed is defined by the following:

1. A scanning device that is employed to scan a region with a beam of light, comprising:
    (a) a light conductive medium configured to convey light from a source, for scanning the region with the light, wherein the light conductive medium comprises an optical fiber;
    (b) a scanning element coupled to the light conductive medium and configured to direct light conveyed through the light conductive medium to the region by scanning the region in one or more desired patterns;
    (c) a driver that is coupled to the scanning element, the driver applying a force to the scanning element causing the scanning element to move so that the light beam scans over the region in the one or more desired patterns; and
    (d) a control that supplies a driving signal to the driver to vary at least one of an amplitude and a direction of the force applied by the driver to the scanning element, the driving signal providing a first plurality of scanning frames to generate a first scanning pattern along an axis and a second plurality of scanning frames to generate a second scanning pattern along the axis, the control comprising software that, when executed, causes the control to generate the first scanning pattern along the axis with the first plurality of scanning frames and the second scanning pattern along the axis with the second plurality of scanning frames, the first plurality of scanning frames causing the driver to move the scanning element in a first mode at a resonant or near-resonant condition to provide the first scanning pattern along the axis during each of the first plurality of scanning frames in order to achieve a first function, the second plurality of scanning frames causing the driver to move the same scanning element in a second mode to provide the second scanning pattern and scan a portion of the region with the second scanning pattern along the axis during each of the second plurality of scanning frames in order to achieve a different second function, wherein the second plurality of scanning frames interrupts the first plurality of scanning frames wherein at least one characteristic of the first scanning pattern in the first mode is different from the second scanning pattern in the second mode based on the selected first and second functions.

2. The scanning device of claim 1, wherein the driver applies the force to move the scanning element relative to two generally orthogonal directions.

3. The scanning device of claim 1, wherein the scanning element comprises a movably mounted light reflective surface that is driven by the driver to move, reflecting the light beam toward the region so that the light beam scans the region in the desired pattern.

4. The scanning device of claim 1, wherein the force applied by the driver drives the scanning element generally into a resonant motion during each of the first plurality of scanning frames, so as to achieve at least one of the one or more desired patterns, the resonant motion of the scanning element being interrupted within each of the first plurality of scanning frames by the second plurality of scanning frames.

5. The scanning device of claim 1, wherein the light conductive medium is configured to be coupled to a first source of light during each of the first plurality of scanning frames and to a second source of light during each of the first plurality of scanning frames, the first source producing light that is different than the light produced by the second source.

6. The scanning device of claim 5, wherein the light produced by the first source differs from the light produced by the second source in regard to at least one of:
    (a) an intensity of the light;
    (b) a waveband of the light; or
    (c) a modulation frequency of the light.

7. The scanning device of claim 1, wherein the at least one characteristic of the first scanning pattern that is different in the first mode than the second scanning pattern in the second mode comprises at least one of:
    (a) a scan pattern size;
    (b) a scan pattern shape;
    (c) a scan pattern duration;
    (d) a resolution of the scan pattern; or
    (e) a quality of the light comprising the light beam.

8. The scanning device of claim 1, wherein the control selectively controls a dwell time for scanning the light beam over the region, so that a different dwell time is employed during the first mode than during the second mode.

9. The scanning device of claim 1, further comprising a light detector that receives light from the region, the light detector being configured to connect to a display for displaying an image of the region.

10. The scanning device of claim 1, wherein the first mode is used for at least one function selected from the group of functions consisting of:
    (a) imaging the region;
    (b) monitoring a state of the region;
    (c) providing a therapy with the light beam to the region; and
    (d) diagnosing a condition of the region.

11. The scanning device of claim 1, wherein the second mode is capable of at least one of the functions of:
    (a) imaging the region;
    (b) monitoring a state of the region;
    (c) providing a therapy with the light beam to the region; or
    (d) diagnosing a condition of the region.

12. The scanning device of claim 1, wherein the desired pattern in each of the first mode and the second mode comprises at least one of:
    (a) a generally circular scan;
    (b) a generally elliptical scan;
    (c) a point scan in which the scanning device is illuminating a point;
    (d) a linear scan;
    (e) a propeller scan; or
    (f) a Lissajous scan.

13. The scanning device of claim 1, wherein ends of the light conductive medium have been conditioned to allow the propagation of higher intensities of light without damage, the conditioning utilizing at least one of:
    (a) an end cap;
    (b) an aperture;
    (c) a mechanical polish;
    (d) an optical polish; or
    (e) a hermetic seal.

14. The scanning device of claim 1, further comprising means for monitoring an entry face of the light conductive medium for damage using at least one of:
    (a) video imaging; or
    (b) reflective monitoring.

15. The scanning device of claim 1, further comprising a motion control system for controlling a position of an entry face of the light conductive medium, enabling an alignment of the light conductive medium to be executed by a user.

16. The scanning device of claim 1, wherein a progress of therapy applied with the scanning device is monitored by collecting feedback from a region of interests comprises at least one of:
    (a) infrared radiation;
    (b) an optical polarization; or
    (c) a time of flight measurement.

17. A method for scanning a light beam over a region, comprising the steps of:
    (a) providing light to a scanning element from a first light source for the light beam, the first light source being selected to carry out a first function when scanning the light beam in the region using a first scanning pattern along an axis;
    (b) driving the scanning element in the first scanning pattern along the axis at a resonant or near-resonant condition, to scan the region with the light beam emitting light from the first light source during each of a first plurality of scanning frames;
    (c) providing light to the same scanning element from a second light source for the light beam, the second light source being selected to carry out a second function when scanning the light beam in the region using a second scanning pattern along the axis; and
    (d) driving the same scanning element in the second scanning pattern along the axis during each of a second plurality of scanning frames, so as to scan a portion of the region with the light beam during each of the second plurality of scanning frames, wherein the second plurality of scanning frames interrupts the first plurality of scanning frames and wherein the first scanning pattern along the axis differs in at least one characteristic from the second scanning pattern along the axis based on the selected first and second functions.

18. The method of claim 17, wherein the scanning element comprises a light reflective surface that is pivotally mounted to scan the region with the light beam when the light reflective surface is driven in at least one of the first scanning pattern, or the second scanning pattern.

19. The method of claim 17, further comprising the step of imaging light from the region produced by scanning the region in one of the first scanning pattern and the second scanning pattern.

20. The method of claim 17, wherein the first function comprises at least one of:
    (a) imaging the region;
    (b) providing a therapy to the region with the light beam;
    (c) diagnosing a condition of the region; or
    (d) monitoring the region.

21. The method of claim 17, wherein the second function comprises at least one of:
   (a) imaging the region;
   (b) providing a therapy to the region with the light beam;
   (c) diagnosing a condition of the region; or
   (d) monitoring the region.

22. The method of claim 17, wherein at least one of the steps of driving the scanning element in the first pattern and of driving the scanning element in the second pattern comprises the step of causing the scanning element to move in a resonant condition.

23. The method of claim 17, wherein the at least one characteristic by which the first pattern differs from the second pattern comprises at least one of:
   (a) a size;
   (b) an amplitude in at least one direction;
   (c) a duration;
   (d) a shape;
   (e) a resolution; or and
   (f) a depth.

24. The method of claim 17, further comprising the step of providing a selectively variable dwell time, so that a different dwell time is used for the first scanning mode than for the second scanning mode.

25. The method of claim 17, wherein the steps of driving the light conductive medium in the first scanning mode and the second mode each comprises the step of driving the light conductive medium in at least one of:
   (a) a generally circular scan;
   (b) a generally elliptical scan;
   (c) a point scan in which the scanning device is not moving relative to a point in the region;
   (d) a linear scan;
   (e) a propeller scan; or
   (f) a Lissajous scan.

26. The method of claim 17, further comprising the step of:
   (a) receiving light from the region; and
   (b) in response to the light received, producing an image of the region.

27. The method of claim 26, wherein the light received from the region is provided by the light beam scanning the region during at least one of the first scanning mode or the second scanning mode.

28. The method of claim 26, further comprising the step of scanning a smaller portion of the region during one of the first scanning mode and the second scanning mode than during the other of the first scanning mode and the second scanning mode, to zoom in on the smaller portion as viewed in the image.

29. The method of claim 17, further comprising the step of employing a higher intensity light source for the light beam during at least one of the first scanning mode or the second scanning mode, the higher intensity light source being used to provide a therapy to the region.

30. The method of claim 17, wherein the steps of driving the light conductive medium to scan in at least one of the first scanning mode and the second scanning mode, comprises the step of providing an amplitude modulated drive signal to drive the scanning element, the amplitude modulated drive signal being interrupted between scanning modes.

31. The method of claim 17, wherein at least one of the steps of driving the scanning element to scan comprises the step of directing the scanning element to selectively scan one or more different smaller portions of the region, by controlling a direction and an amplitude of the scanning of the light beam to direct the light beam at each smaller region.

32. The method of claim 17, further comprising the step of interrupting scanning of the region with the light beam at a desired position, to render a diagnostic function, comprising at least one of:
   (a) detecting a fluorescence at the desired position;
   (b) determine one of a fluorescence and phosphorescence lifetime at the desired position;
   (c) conducting a laser-induced fluorescence spectroscopic analysis at the desired position;
   (d) conducting a white light reflectance spectroscopic analysis at the desired position;
   (e) conducting a Raman spectroscopic analysis at the desired position;
   (f) conducting a range finding to determine a range to the desired position;
   (g) conducting an optical coherence reflectance depth measurement at the desired position; or
   (h) conducting a multi-photon investigation at the desired position.

33. The method of claim 17, further comprising the step of interrupting scanning of the region with the light beam at a desired position, to render a therapeutic function, and carrying out at least one of:
   (a) performing an ablation at the desired position;
   (b) causing heating at the desired position;
   (c) carrying out photodynamic therapy at the desired position;
   (d) causing photo-ionization at the desired position;
   (e) causing photo-polymerization at the desired position;
   (f) causing photo-acoustic vibration at the desired position; or
   (g) causing photo-activating of molecules at the desired position.

34. The method of claim 17, wherein at least one of the first scanning mode and the second scanning mode is employed for one of
   (a) a laser illumination optoporation procedure; and
   (b) a vision modification procedure.

35. The method of claim 17, further comprising the step of driving the scanning element in one or more additional scanning modes to provide additional functions in regard to the region being scanned with a light beam, at least one characteristic of the each additional scanning mode differing from a corresponding characteristic in each other scanning mode.

36. The method of claim 17, further comprising the step of employing an extrinsic chromophore to aid light absorption.

37. The method of claim 17, further comprising the step of employing an extrinsic fluorophore to aid optical diagnosis.

38. The scanning device of claim 1, wherein causing the driver to move the same scanning element in the second mode during the second plurality of scanning frames in order to achieve the different second function comprises moving the scanning element to a stopped position within each of the first plurality of scanning frames to achieve non-resonant scanning with each of the second plurality of scanning frames for the different second function.

39. The method of claim 17, wherein driving the same scanning element in the second scanning mode for each of the second plurality of scanning frames comprises moving the scanning element to a stopped position within each of the first plurality of scanning frames to achieve non-resonant scanning with said each of the second plurality of scanning frames for the second function.

* * * * *

UNITED STATES PATENT AND TRADEMARK OFFICE
CERTIFICATE OF CORRECTION

PATENT NO.       : 8,537,203 B2
APPLICATION NO. : 12/088057
DATED            : September 17, 2013
INVENTOR(S)      : Seibel et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1185 days.

Signed and Sealed this
Fifteenth Day of September, 2015

Michelle K. Lee
*Director of the United States Patent and Trademark Office*